US012678104B2

(12) United States Patent
Single et al.

(10) Patent No.: US 12,678,104 B2
(45) Date of Patent: Jul. 14, 2026

(54) NEURAL RECORDING WITH STIMULUS CROSSTALK COMPENSATION

(71) Applicant: Saluda Medical Pty Ltd, Artarmon (AU)

(72) Inventors: Peter Scott Vallack Single, Artarmon (AU); James Hamilton Wah, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 890 days.

(21) Appl. No.: 17/998,498

(22) PCT Filed: May 18, 2021

(86) PCT No.: PCT/AU2021/050458
§ 371 (c)(1),
(2) Date: Nov. 11, 2022

(87) PCT Pub. No.: WO2021/232091
PCT Pub. Date: Nov. 25, 2021

(65) Prior Publication Data
US 2023/0200738 A1 Jun. 29, 2023

(30) Foreign Application Priority Data
May 18, 2020 (AU) ................................ 2020901586

(51) Int. Cl.
*A61B 5/00* (2006.01)
*A61B 5/30* (2021.01)
*A61B 5/388* (2021.01)

(52) U.S. Cl.
CPC .............. *A61B 5/7203* (2013.01); *A61B 5/30* (2021.01); *A61B 5/388* (2021.01)

(58) Field of Classification Search
CPC ....... A61B 5/7203; A61B 5/246; A61B 5/369; A61B 5/372; A61B 5/377; A61B 5/388;
(Continued)

(56) References Cited

U.S. PATENT DOCUMENTS 5,758,651 A 6/1998 Nygard et al.
5,913,882 A 6/1999 King
(Continued)

FOREIGN PATENT DOCUMENTS

EP 2278329 A1 1/2011
WO WO1994014376 A1 7/1994
(Continued)

OTHER PUBLICATIONS

Extended European Search Report in EP Application No. 21808705.4, dated Jun. 4, 2024, 9 pages.
(Continued)

*Primary Examiner* — Puya Agahi
(74) *Attorney, Agent, or Firm* — Barnes & Thornburg LLP

(57) ABSTRACT

A device for recording evoked neural responses, comprising one or more stimulus electrodes and one or more sense electrodes. The device has a stimulus source for providing a stimulus to be delivered from the stimulus electrodes to a neural pathway in order to give rise to an evoked action potential on the neural pathway. The device has measurement circuitry for recording a neural compound action potential signal sensed at the sense electrodes. Crosstalk cancellation circuitry is configured to produce a stimulus crosstalk cancellation signal, and is configured to inject the stimulus crosstalk cancellation signal into the measurement circuitry. The stimulus crosstalk cancellation signal is con-
(Continued)

figured to cancel a stimulus crosstalk voltage arising upon the one or more sense electrodes as a result of delivery of the stimulus.

28 Claims, 20 Drawing Sheets

(58) Field of Classification Search
CPC ....... A61B 5/294; A61B 5/311; A61B 5/4082; A61B 5/6868; A61B 5/6877; A61N 1/0551
See application file for complete search history.

(56) References Cited

U.S. PATENT DOCUMENTS

| | | | |
|---|---|---|---|
| 6,493,576 | B1 | 12/2002 | Dankwart-Eder |
| 9,386,934 | B2 | 7/2016 | Parker et al. |
| 10,842,996 | B2 | 11/2020 | Baru et al. |
| 2007/0225767 | A1 | 9/2007 | Daly et al. |
| 2010/0222844 | A1 | 9/2010 | Troosters et al. |
| 2019/0030339 | A1 | 1/2019 | Baru et al. |
| 2019/0307341 | A1 | 10/2019 | Parker et al. |
| 2020/0100731 | A1 | 4/2020 | Bhadra et al. |
| 2022/0072307 | A1* | 3/2022 | Melman ............. A61N 1/36039 |

FOREIGN PATENT DOCUMENTS

| | | | |
|---|---|---|---|
| WO | WO2004021885 | A1 | 3/2004 |
| WO | WO2010114655 | A1 | 10/2010 |
| WO | WO2012056882 | A1 | 5/2012 |
| WO | WO2012155183 | A1 | 11/2012 |
| WO | WO2012155190 | A1 | 11/2012 |
| WO | WO2014071445 | A1 | 5/2014 |
| WO | WO2014071446 | A1 | 5/2014 |
| WO | WO2015168735 | A1 | 11/2015 |
| WO | WO2017219096 | | 12/2017 |
| WO | WO2018160271 | A1 | 9/2018 |
| WO | WO2019162878 | A1 | 8/2019 |
| WO | WO2019177798 | A1 | 9/2019 |
| WO | WO2020082118 | | 4/2020 |
| WO | WO2020082126 | A1 | 4/2020 |
| WO | WO2020082128 | A1 | 4/2020 |
| WO | WO2020205234 | A1 | 10/2020 |

OTHER PUBLICATIONS

Kent, Alexander Rafael, Characterization of Evoked Potentials During Deep Brain Stimulation in the Thalamus. Dissertation, Duke University, 2013, Retrieved from https://dukespace.lib.duke.edu/dspace/handle/10161/8195 on Jul. 16, 2024, 320 pages.

Kevin C Mcgill et al., "On the Nature and Elimination of Stimulus Artifact in Nerve Signals Evoked and Recorded Using Surface Electrodes", IEEE Transactions on Biomedical Engineering, IEEE, USA, vol. BME-29, No. 2, Feb. 1, 1982 (Feb. 1, 1982), pp. 129-137.

Mendrela Adam E et al., A Bidirectional Neural Interface Circuit With Active Stimulation Artifact Cancellation and Cross-Channel Common-Mode Noise Suppression, IEEE Journal of Solid-State Circuits, IEEE, USA, vol. 51, No. 4, Apr. 1, 2016 (Apr. 1, 2016), pp. 955-965.

Blum, A. R., "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012, 132 pages.

Stanslaski et al., "Design and Validation of a Fully Implantable, Chronic, Closed-Loop Neuromodulation Device With Concurrent Sensing and Stimulation", IEEE Transactions on Neural Systems and Rehabilitation Engineering, Jul. 2012, Date of Publication: Jan. 23, 2012, vol. 20, No. 4, pp. 410-421.

Zhou et al., "A High Input Impedance Low Noise Integrated Front-End Amplifier for Neural Monitoring", IEEE Transactions on Biomedical Circuits and Systems, 2016, vol. 10, No. 6, pp. 1079-1086.

* cited by examiner

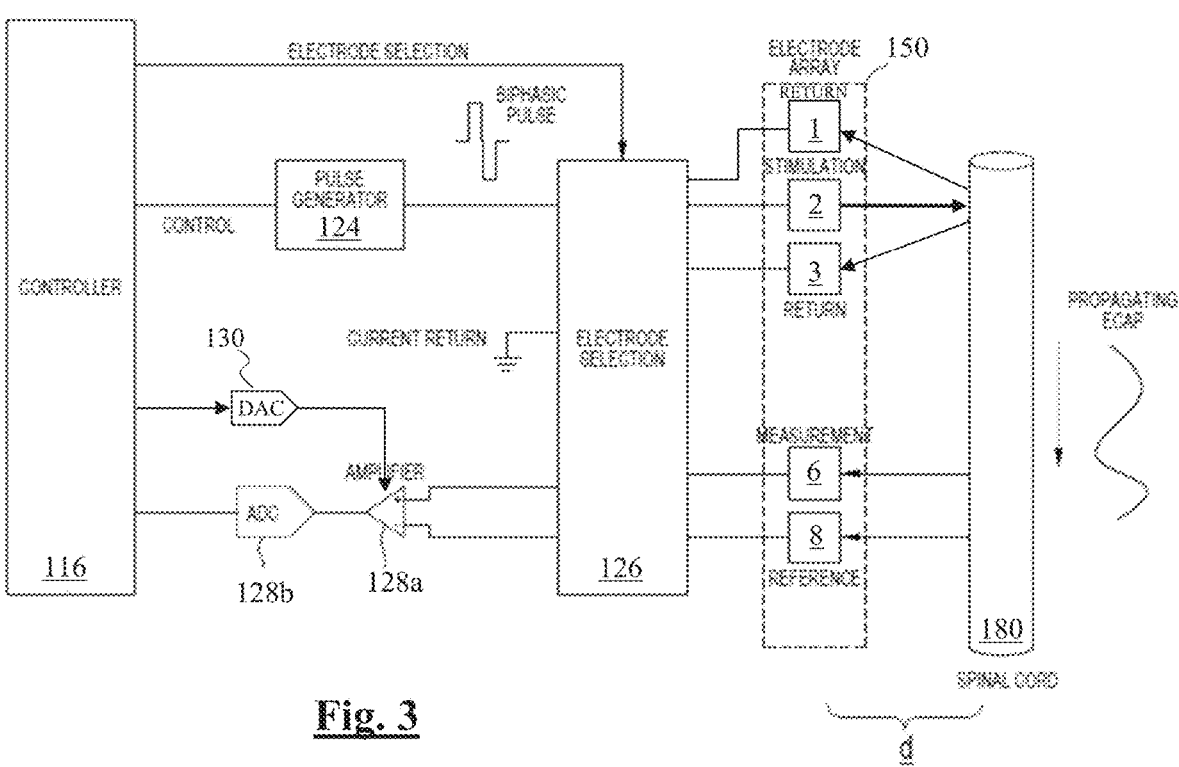
Fig. 3
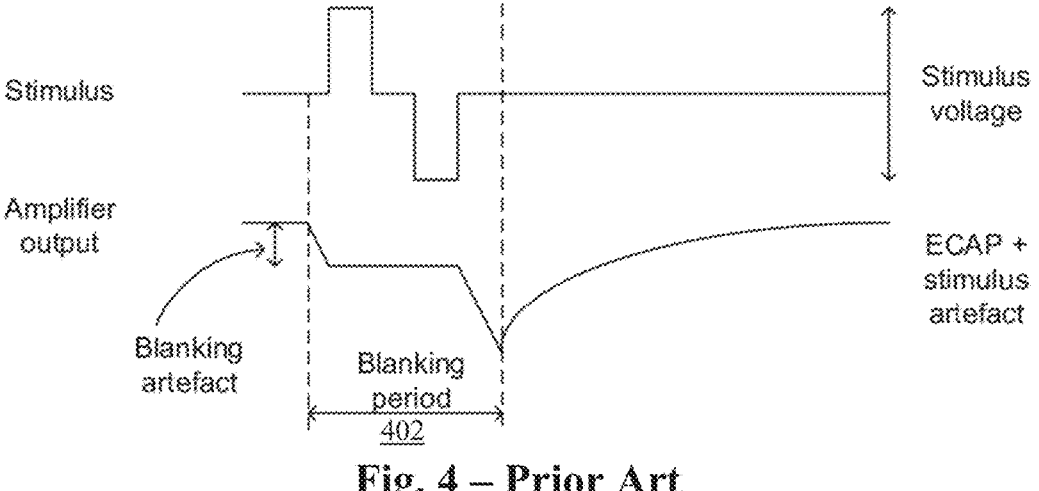
Fig. 4 – Prior Art

502  503                550              506              508

Stimulator                                    Amplifier

Stimulator            Tissue            Amplifier

Stimulus current waveform

Compensation voltage in

1kΩ    9kΩ

702

704

Rec+

Rec-

Out

Rec+

704
10×

804
10×

ADC
806

Compensating
signal

Voltage on stim and return electrodes

Voltage on recording electrodes

Rec+

Rec-

A

B

2510

U1

U2

U3

Voltage at electrode

Switch    Closed
          Open

Voltage on capacitor

Amp output

Rec+

To amplifier

NEURAL RECORDING WITH STIMULUS CROSSTALK COMPENSATION

CROSS-REFERENCE TO RELATED APPLICATIONS

This application is a U.S. National Stage Patent Application of PCT Application No. PCT/AU2021/050458, filed May 18, 2021 which claims the benefit of Australian Provisional Patent Application No. 2020901586 filed May 18, 2020, which is incorporated herein by reference.

TECHNICAL FIELD

The present invention relates to measurement of compound action potentials evoked by neurostimulation, and in particular the invention relates to compensating for the effect of stimulus artefact upon measurement circuitry so as to facilitate operation of measurement circuitry during application of a stimulus.

BACKGROUND OF THE INVENTION

There are a range of situations in which it is desirable to apply neural stimuli in order to give rise to an evoked compound action potential (ECAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord, referred to as spinal cord stimulation (SCS). Neuromodulation systems typically comprise an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and the generation of propagating action potentials. The fibres being stimulated in this way inhibit the transmission of pain from that segment in the spinal cord to the brain. To sustain the pain relief effects, stimuli are applied substantially continuously, for example at a frequency in the range of 50-100 Hz.

Neuromodulation may also be used to stimulate efferent fibres, for example to induce motor functions. In general, the electrical stimulus generated in a neuromodulation system triggers one or more neural action potentials, which then have either an inhibitory or excitatory effect. Inhibitory effects can be used to modulate an undesired process such as the transmission of pain, or excitatory effects may for example cause a desired effect such as the contraction of a muscle.

There are a range of circumstances in which it is desirable to obtain an electrical measurement of an ECAP evoked on a neural pathway by an electrical stimulus applied to the neural pathway. However, this can be a difficult task as an observed ECAP signal will typically have a maximum amplitude of a few tens of microvolts or less, whereas a stimulus applied to evoke the ECAP is typically several volts. Electrode artefact usually results from the stimulus, and manifests as a decaying output of several millivolts or hundreds of microvolts throughout the time that the ECAP occurs, presenting a significant obstacle to isolating the much smaller ECAP of interest. As the neural response can be contemporaneous with the stimulus and/or the stimulus artefact, ECAP measurements present a difficult challenge of implant design. In practice, many non-ideal aspects of a circuit lead to artefact, and as these mostly have a decaying exponential characteristic which can be of either positive or negative polarity, identification and elimination of sources of artefact can be laborious. A number of approaches have been proposed for recording an ECAP, including those of King (U.S. Pat. No. 5,913,882), Nygard (U.S. Pat. No. 5,758,651), Daly (US Patent Application No. 2007/0225767) and the present Applicant (U.S. Pat. No. 9,386, 934).

Evoked responses are less difficult to detect when they appear later in time than the artefact, or when the signal-to-noise ratio is sufficiently high. The artefact is often restricted to a time of 1-2 ms after the stimulus and so, provided the neural response is detected after this time window, data can be obtained. This is the case in surgical monitoring where there are large distances between the stimulating and recording electrodes so that the neural response propagation time from the stimulus site to the recording electrodes exceeds 2 ms. However, neurostimulation implants are by necessity compact devices. To characterize responses evoked by a single implant such as responses from the dorsal columns to SCS, for example, high stimulation currents and close proximity between electrodes are required, and therefore the measurement process must overcome contemporaneous stimulus artefact directly, greatly exacerbating the difficulty of neural measurement.

Similar considerations can arise in deep brain stimulation where it can be desirable to stimulate a neural structure and immediately measure the evoked compound action potential produced in that structure before the neural response propagates elsewhere in the brain. Artefact remains a significant obstacle to measurement of neural responses proximal to the stimulus location, with the consequence that most neurostimulation implants do not take any measurements whatsoever of neural responses evoked by the implant's stimuli.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a device for recording evoked neural responses, the device comprising:
- a plurality of electrodes including one or more nominal stimulus electrodes and one or more nominal sense electrodes;
- a stimulus source for providing a stimulus to be delivered from the one or more stimulus electrodes to a neural pathway in order to give rise to an evoked action potential on the neural pathway;

measurement circuitry for recording a neural compound action potential signal sensed at the one or more sense electrodes; and crosstalk cancellation circuitry configured to produce a stimulus crosstalk cancellation signal, the crosstalk cancellation circuitry further configured to inject the stimulus crosstalk cancellation signal into the measurement circuitry, the stimulus crosstalk cancellation signal being configured to cancel a stimulus crosstalk voltage arising upon the one or more sense electrodes as a result of delivery of the stimulus.

According to a second aspect the present invention provides a method for recording evoked neural responses, the method comprising:

delivering a stimulus from one or more stimulus electrodes to a neural pathway in order to give rise to an evoked action potential on the neural pathway;

recording, with measurement circuitry, a neural compound action potential signal sensed at one or more sense electrodes; and injecting a stimulus crosstalk cancellation signal into the measurement circuitry, the stimulus crosstalk cancellation signal being configured to cancel a stimulus crosstalk voltage arising upon the one or more sense electrodes as a result of delivery of the stimulus.

In some embodiments, the stimulus crosstalk cancellation signal is injected into the measurement circuitry prior to analog-to-digital conversion of the neural compound action potential signal. In some embodiments the stimulus crosstalk cancellation signal is injected into the measurement circuitry prior to high gain amplification of the neural compound action potential signal.

It is to be understood herein that terms such as "cancel" and "cancellation" encompass partial or imperfect cancellation. For example cancellation of the stimulus crosstalk voltage may comprise a partial cancellation or partial reduction of the stimulus crosstalk voltage as experienced by the measurement circuitry, as compared to a level of stimulus crosstalk experienced by the measurement circuitry when the crosstalk cancellation circuitry is absent or deactivated, so as to partially compensate for stimulus crosstalk. The degree of cancellation achieved is preferably sufficient to avoid non-linearity, clipping or saturation of the measurement circuitry, or may merely be used to reduce the dynamic range of the signal so it can be digitized with an ADC with lower resolution.

In some embodiments of the invention, the stimulus may comprise one or more stimulus phases, and each stimulus phase may comprise a pulse of constant current. In such embodiments, the pulse of constant current may be delivered by a first stimulus electrode and a return electrode may be driven by a virtual ground circuit which seeks to drive a sense electrode voltage to ground. In these embodiments, the stimulus crosstalk cancellation signal may be configured to take a respective constant value during each stimulus phase, the constant value of the stimulus crosstalk cancellation signal being selected to cancel the stimulus crosstalk voltage arising upon the one or more sense electrodes as a result of delivery of the pulse of constant current. Such embodiments may be particularly useful in situations where such virtual ground feedback is applied or more generally may be useful where constant compensation is sufficient to avoid clipping in the measurement circuitry.

Further embodiments of the invention may additionally or alternatively provide for non-constant compensation, in order to cancel a non-constant stimulus crosstalk voltage arising upon the one or more sense electrodes as a result of delivery of the stimulus. For example a non-constant stimulus crosstalk voltage may occur in each stimulus phase when a constant current stimulus phase is returned by a stimulus return electrode which is connected directly to ground, and/or may occur when each stimulus phase comprises a pulse of varying current, and/or may occur when each phase comprises an applied voltage pulse. Additionally or alternatively, non-constant compensation may be applied in order to cancel a non-constant stimulus crosstalk arising as a result of use of one or more sense electrodes to pass current during the stimulus phase, for example one or more sense electrodes may serve as the stimulus electrode during the stimulus phase.

The stimulus crosstalk cancellation signal may comprise a voltage signal, and/or a current signal.

Some embodiments of the invention, whether employing constant compensation or non-constant compensation in each phase, may configure the stimulus crosstalk cancellation signal to take a value or to vary during a stimulus phase in accordance with measurements of stimulus crosstalk occurring in a previous stimulus, in a previous stimulus phase, or at a previous time within the same stimulus phase. In such embodiments the measurements of stimulus crosstalk may be obtained from the sense electrodes using an analog to digital converter (ADC).

Additionally or alternatively, some embodiments of the invention may configure the stimulus crosstalk cancellation signal to take a value or profile during a stimulus phase in accordance with predictions of expected stimulus crosstalk, the predictions being made using a model. The model may be updated iteratively over time based on observed performance of the stimulus crosstalk cancellation signal over multiple stimuli. Use of a model of the crosstalk signal may also be advantageous in avoiding overfitting causing cancellation of the ECAP signal itself.

In some embodiments the model for predicting crosstalk may be derived from a circuit model of the electrodes and attached circuitry, and for example may include one or more of: a linear ramp; a decaying exponential; a step or impulse response of a fractional pole element; a step or impulse response of a fractional pole element in series with a resistor; template waveforms obtained from recordings of crosstalk; functions fitted to template waveforms obtained from recordings of crosstalk; and sum of one or more of these elements.

Some embodiments of the invention may additionally or alternatively configure the stimulus crosstalk cancellation signal so as to cancel predicted or observed components of stimulus crosstalk arising in the measurement circuitry as a result of resistive coupling via tissue between the electrodes.

Further embodiments of the invention may additionally or alternatively configure the stimulus crosstalk cancellation signal so as to cancel predicted or observed components of stimulus artefact arising in the measurement circuitry as a result of accumulated charge in electrode-tissue interface layers as a function of position along each electrode of the plurality of electrodes. Such embodiments for example may configure the stimulus crosstalk cancellation signal so as to cancel predicted or observed components of stimulus artefact arising in the measurement circuitry as a result of accumulated charge in passive electrodes, the passive electrodes being electrodes other than the stimulus electrodes and sense electrodes. Such embodiments for example may configure the stimulus crosstalk cancellation signal so as to cancel predicted or observed components of stimulus artefact arising in the measurement circuitry as a result of accumulated charge only in one, or a small number of, passive electrode(s) closest to the stimulus electrode(s). Alternatively, such embodiments may configure the stimulus crosstalk cancellation signal so as to cancel predicted or observed components of stimulus artefact arising in the measurement circuitry as a result of accumulated charge in all passive electrodes.

Some embodiments of the invention may additionally or alternatively configure the stimulus crosstalk cancellation signal so as to cancel predicted or observed components of stimulus artefact arising in the measurement circuitry as a result of accumulated charge in electrode-tissue interface layers as a function of position along one or more of the stimulus electrodes.

Some embodiments of the invention may additionally or alternatively configure the stimulus crosstalk cancellation signal so as to cancel predicted or observed components of stimulus artefact arising in the measurement circuitry as a result of non-infinite common-mode rejection of amplifier ground signal variations caused by accumulated charge in electrode-tissue interface layers of a stimulus return electrode. Some embodiments of the invention may additionally or alternatively configure the stimulus crosstalk cancellation signal so as to cancel predicted or observed components of stimulus artefact arising in the measurement circuitry as a result of finite input impedance of the measurement circuitry causing a voltage to appear at the electrode-tissue interface.

In some embodiments of the invention, the measurement circuitry may comprise a measurement amplifier configured to obtain a single-ended recording of a neural compound action potential signal sensed at one sense electrode. In such embodiments, the sense electrode may be connected to a first input of the measurement amplifier, and a second input of the measurement amplifier may be connected to a midpoint of a resistive chain, the resistive chain extending between an output of the measurement amplifier and a stimulus crosstalk cancellation voltage injection input. In such embodiments, a ratio R of resistance either side of the midpoint in the resistive chain may be used to derive a desired stimulus crosstalk cancellation signal, by multiplying a measured or predicted stimulus crosstalk by R.

In some embodiments of the invention, the measurement circuitry may comprise a measurement amplifier configured to obtain a differential recording of a neural compound action potential signal sensed at two sense electrodes. In such embodiments a first input of the differential amplifier may be connected to an output of the differential amplifier via a feedback element, and a second input of the differential amplifier may be resistively connected to a stimulus crosstalk voltage injection input. Each sense electrode may be connected to a respective input of the measurement amplifier via respective input buffer amplifiers.

In some embodiments of the invention, the measurement circuitry may be blanked for some portion or portions of a period in which the stimulus crosstalk voltage arises, whereby during blanking some or all of the measurement circuitry is disconnected from the sense electrodes, whereby during blanking an output of the measurement circuitry does not carry useful measurement information but also does not suffer from stimulus crosstalk. For example, the measurement circuitry may be blanked during one or more stimulus transients, referred to herein as transient blanking. Transient blanking may be imposed during one or more of an onset of a stimulus phase and cessation of a stimulus phase, for one or more anodic stimulus phase(s) and/or for one or more cathodic stimulus phase(s). Transient blanking may be imposed for example for a period in the range of 10-50 μs either side of a stimulus transient. Noting that a stimulus phase width may be around 0.5-1 ms, such embodiments may thus provide for the measurement circuitry to be unblanked for 80-95% of the duration of each stimulus phase, while being blanked to avoid exposure to stimulus transients, allowing for evoked neural responses to be observed for a significant portion of the stimulus period while avoiding clipping.

Additionally or alternatively, the measurement circuitry may be blanked for one or more entire stimulus phases. For example the stimulus may be configured so that one or more initial stimulus phases are below a recruitment threshold, for example as described in PCT/AU2019/051151. In such embodiments, no neural response would be expected to be recruited during such initial stimulus phases, and so it may thus be preferable to not expose the measurement circuitry to stimulus crosstalk at such times. The measurement circuitry may thereafter be selectively unblanked during a later portion of the stimulus based on a predetermined phase which is expected to recruit a neural response. In such embodiments the reduced period of application of stimulus crosstalk cancellation may provide a power saving.

Alternatively the measurement circuitry may be kept blanked during an initial portion of the stimulus, and thereafter may be unblanked at a time which is adaptively controlled based on one or more past observations of time(s) at which neural responses arise relative to the stimulus. In such embodiments the initial portion of the stimulus during which blanking is imposed may comprise less than one stimulus phase or more than one stimulus phase. The portion of the stimulus during which the measurement circuitry is unblanked may comprise less than one stimulus phase or more than one stimulus phase.

In some embodiments of the invention, the measurement circuitry may be unblanked throughout an entire duration of the stimulus. Additionally or alternatively, the measurement circuitry may remain continuously unblanked during a period of time encompassing at least a final phase of the stimulus and a post-stimulus recording period of interest.

In some embodiments of the invention, the recording of the neural compound action potential signal may comprise a single contiguous recording.

Alternatively, for example in embodiments utilising transient blanking, the recording of the neural compound action potential signal may comprise a plurality of discontinuous recorded segments. An original state of the plurality of recorded segments may provide sufficient recruitment information, for example ECAP amplitude may be determined from such recorded segments simply by a peak-to-peak analysis of available data of the recording. Alternatively a segmented matched filter ECAP detector having segments corresponding temporally to the recorded segments, may be applied to the recorded segments to determine recruitment information. Additionally or alternatively, a plurality of recorded segments may be post-processed such as by interpolation or fitting in order to estimate a neural response profile during blanking periods in between the recorded segments, to further understand an efficacy of the stimulus. Such embodiments may be particularly advantageous where a stimulation frequency is high, such as hundreds of Hz, thousands of Hz or tens of thousands of Hz. At such high stimulation rates the typical 1-2 ms duration of a single evoked ECAP may temporally overlap with more than one stimulus, and so some embodiments of the present invention may enable a continuous or segmented recording of the ECAP to be obtained throughout the course of such multiple stimuli.

In some embodiments of the invention, the recording of the neural compound action potential signal may be processed in order to assess an efficacy of the stimulus, and/or to assess efficacy of a sequence of stimuli. For example, an amplitude of an ECAP observed in the recording may be determined by such processing. The assessed stimulus efficacy may in turn be used to control application of a subsequent stimulus by use of a suitable feedback loop. Notably, embodiments obtaining a neural recording both during and after application of the stimulus may provide improved quality ECAP recordings, as compared to recordings obtained only after cessation of the stimulus. Such improved quality ECAP recordings in turn may lead to improved operation and therapeutic effect of a feedback loop.

In some embodiments of the invention, measuring the neural response may be done on the same electrode as is delivering the stimulation. That is to say, in such embodiments the one or more nominal stimulus electrodes also serve as the one or more nominal sense electrodes. Such embodiments are advantageous in allowing for rapid detection of any recruited neural response, noting that the finite conduction velocity of neural responses necessarily results in the neural response arising on more distant electrodes at a later time. In alternative embodiments, measuring the neural response may be done on a nearby non-stimulating electrode, whereby the one or more nominal stimulus electrodes are distinct from the one or more nominal sense electrodes.

In some embodiments, further cancellation of stimulus crosstalk may be applied in the digital domain after analog-to-digital conversion.

In some embodiments the device is an implantable device.

According to a further aspect the present invention provides a non-transitory computer readable medium for performing the method of the second aspect, comprising instructions which, when executed by one or more processors, causes performance of the said steps.

In some embodiments, the measurement circuitry may further be configured for recording a pre-activation neural response to a stimulus, such as a membrane potential pre-polarisation arising from application of a sub-threshold stimulus.

BRIEF DESCRIPTION OF THE DRAWINGS

An example of the invention will now be described with reference to the accompanying drawings, in which:

FIG. 3 is a schematic illustrating interaction of the implanted stimulator with a nerve;

FIG. 4 depicts simplified waveforms of a prior art blanked ECAP recording system;

FIG. 5b depicts an electrical model of the configuration of FIG. 5a;

DESCRIPTION OF THE PREFERRED EMBODIMENTS

Figure 1:
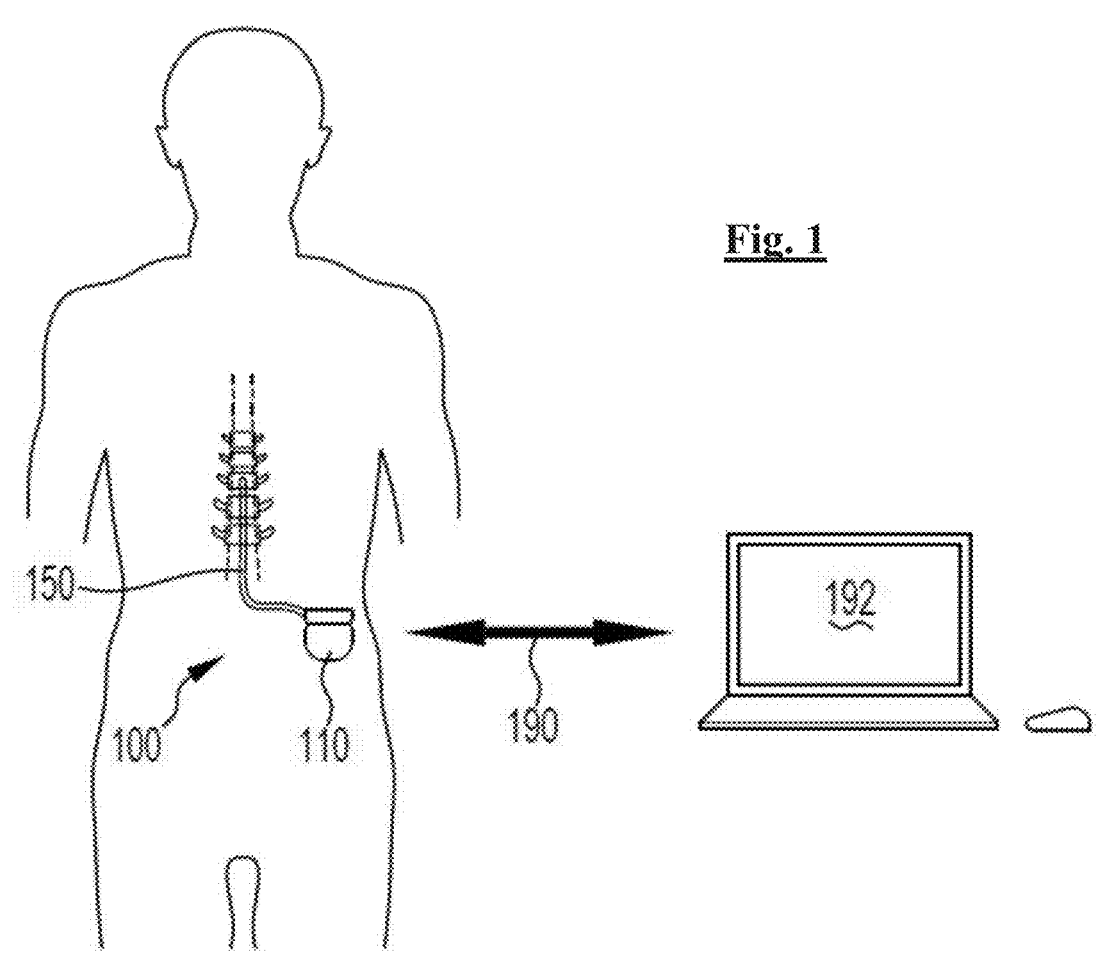
FIG. 1 schematically illustrates an implanted spinal cord stimulator in accordance with one embodiment of the invention.

FIG. 1 schematically illustrates an implanted spinal cord stimulator 100. Stimulator 100 comprises an electronics module 110 implanted at a suitable location in the patient's lower abdominal area or posterior superior gluteal region, and an electrode assembly 150 implanted within the epidural space and connected to the module 110 by a suitable lead. Numerous aspects of operation of implanted neural device 100 are reconfigurable by an external control device 192. Moreover, implanted neural device 100 serves a data gathering role, with gathered data being communicated to external device 192 via any suitable transcutaneous communications channel 190.

Figure 2:
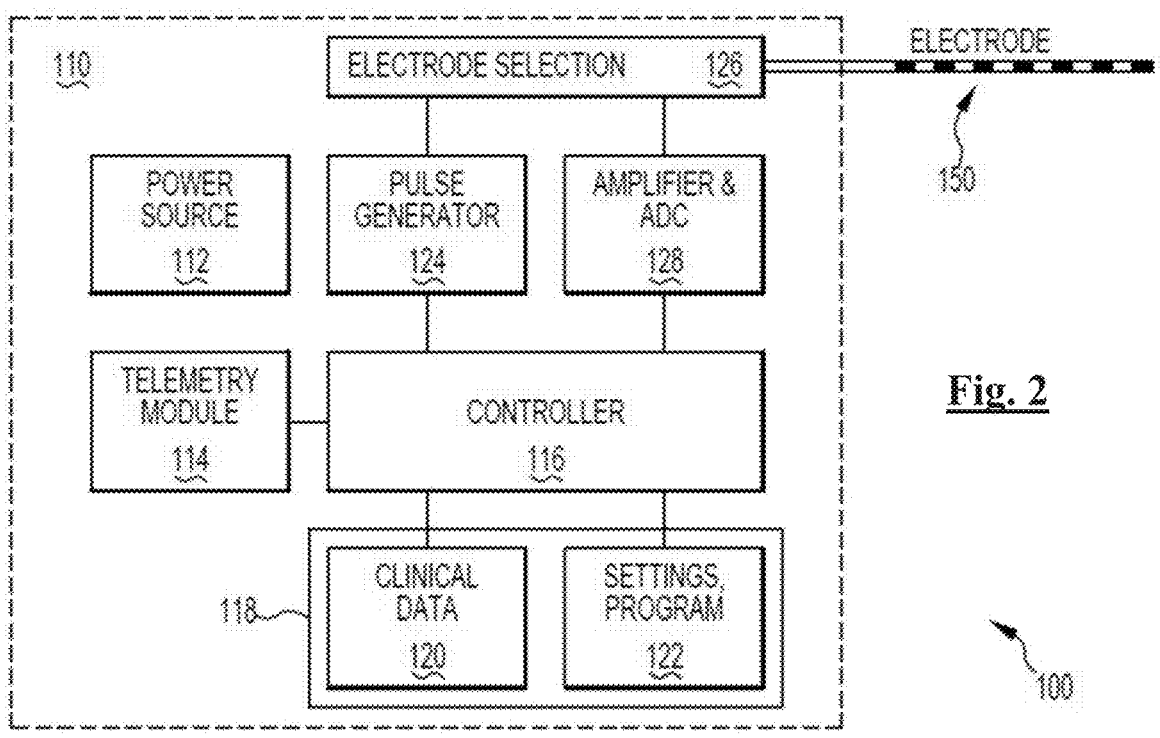
FIG. 2 is a block diagram of the implanted neurostimulator of FIG. 1.

FIG. 2 is a block diagram of the implanted neurostimulator 100. Module 110 contains a battery 112 and a telemetry module 114. In embodiments of the present invention, any suitable type of transcutaneous communication 190, such as infrared (IR), electromagnetic, capacitive and inductive transfer, may be used by telemetry module 114 to transfer power and/or data between an external device 192 and the electronics module 110. Module controller 116 has an associated memory 118 storing patient settings 120, control programs 122 and the like. Controller 116 controls a pulse generator 124 to generate stimuli in the form of current pulses in accordance with the patient settings 120 and control programs 122. Electrode selection module 126 switches the generated pulses to the appropriate electrode(s) of electrode array 150, for delivery of the current pulse to the tissue surrounding the selected electrode(s). Measurement circuitry 128 is configured to capture measurements of neural responses sensed at sense electrode(s) of the electrode array as selected by electrode selection module 126.

FIG. 3 is a schematic illustrating interaction of the implanted stimulator 100 with a nerve 180, in this case the spinal cord however alternative embodiments may be positioned adjacent any desired neural tissue including a peripheral nerve, visceral nerve, parasympathetic nerve or a brain structure. The pulse generator 124 produces a suitable stimulus pulse, which in FIG. 3 is shown as a biphasic pulse, although alternative embodiments of the invention may utilise a triphasic pulse or other multiphasic pulse for example in accordance with the teachings of in International Patent Publication No. WO 2017/219096 by the present applicant, the content of which is incorporated herein by reference. Electrode selection module 126 selects a stimulation electrode 2 of electrode array 150 to deliver the electrical current pulse to surrounding tissue including nerve 180, and selects return electrodes 1 and 3 for stimulus current recovery to maintain a zero net charge transfer. In this manner electrode selection module 126 effects tripolar stimulation via electrodes 1, 2, 3, for example in accordance with the teachings of the above-noted WO 2017/219096, and/or in accordance with the teachings of International Patent Application No. PCT/AU2019/051151 by the present applicant, the content of which is incorporated herein by reference. Alternative embodiments may utilise bipolar stimulation by use of two electrodes.

Delivery of an appropriate stimulus to the nerve 180 evokes a neural response comprising a compound action potential which will propagate along the nerve 180 as illustrated, for therapeutic purposes which in the case of a spinal cord stimulator for chronic pain might be to create paraesthesia at a desired location. To this end the stimulus electrodes are used to deliver stimuli at any therapeutically suitable frequency, for example 30 Hz, although other frequencies may be used including as high as the kHz range, and/or stimuli may be delivered in a non-periodic manner such as in bursts, or sporadically, as appropriate for the patient. To fit the device, a clinician typically applies stimuli of various configurations which seek to produce a sensation that is experienced by the user as a paraesthesia, or generally to provide a desirable therapy. When a stimulus configuration is found which evokes paraesthesia, which is in a location and of a size which is congruent with the area of the user's body affected by pain, the clinician nominates that configuration for ongoing use.

The device 100 is further configured to sense the existence and intensity of compound action potentials (CAPs) propagating along nerve 180, whether such CAPs are evoked by the stimulus from electrodes 2 and 4, or otherwise evoked. To this end, any electrodes of the array 150 may be selected by the electrode selection module 126 to serve as measurement electrode 6 and measurement reference electrode 8. Signals sensed by the measurement electrodes 6 and 8 are passed to measurement circuitry comprising one or more amplifiers 128*a*, which for example may operate in accordance with the teachings of International Patent Application Publication No. WO2012155183 by the present applicant, the content of which is incorporated herein by reference. The output of the amplifier(s) 128*a* is then digitised by analog to digital converter 128*b* and passed to the controller 116. Nevertheless, artefact remains a significant obstacle to measurement of neural responses proximal to the stimulus location. The present Applicant has previously presented a model of the neurostimulation environment, in International Patent Application No. PCT/AU2019/051160, the contents of which are incorporated herein by reference.

Recording evoked compound action potentials thus requires the delivery of an electrical stimulus, and the recording of electrical potentials produced by the stimulated nerves. This is challenging because the evoked potentials can be much smaller than the stimuli, for example around six orders of magnitude smaller. Unless special measures are taken, the stimulus obscures the response. For example, in spinal cord stimulation, where a distance d between the electrode array 150 and the nerve 180 can be several millimetres, a therapeutically optimal stimulus applied by electrodes 1, 2, 3 can be on the order of 10 volts, while the evoked potential observed on the measurement electrodes 6, 8 can be on the order of 10 microvolts. The evoked responses generally must be recorded very quickly after the stimulus, as the duration of the evoked responses is typically quite short, the recording electrodes 6,8 are close to the stimulus electrodes 1, 2, 3 due to the limited size of the implanted device, and the conduction velocity of the nerve 180 is quite high (e.g. in the range 15-70 m·s$^{-1}$). As a result, depending on the electrode configuration and the conduction velocity of the nerves stimulated, a 1 millisecond duration of evoked responses is typical. Building a system to directly digitise a waveform with this dynamic range is impractical; in this example, resolving the ECAP to just 4 bits of resolution would require a signal chain and ADC with no less than 24 bits of effective resolution, sampling on the order of 1 kHz. This is not practical with present technology, particularly for a compact implantable device with limited power budget.

Existing ECAP amplifiers avoid this problem using blanking. Blanking involves disconnecting the recording amplifier(s) 128a, which have high gain, from the recording electrodes 6, 8 during the stimulus. Shortly after the stimulus is completed, the amplifiers 128a are reconnected, and thereafter the signal from the recording electrodes 6, 8 is recorded, including the ECAP and any extant artefact. The blanking period must be sufficiently long that the extant artefact has reduced sufficiently after cessation of the stimulus that the amplifiers 128a are not saturated. However, a consequence of blanking is that any component of neural response which occurs during the blanking period is not recorded. Depending on the length of the blanking period, the conduction velocity of the nerve fibres recruited by the stimulus, and the physical extent (e.g. length) of the recording electrode array 150, the imposition of such a blanking period can result in a significant loss of information. FIG. 4 depicts simplified waveforms of such a blanked ECAP recording system. For the blanking period 402 surrounding the stimulus, the amplifier input is disconnected from the recording electrodes, so the amplifier output carries no useful signal. After reconnection, the amplifier output takes some time to come out of blanking. Only after this time does the amplifier output actually represent the ECAP and stimulus artefact present at the recording electrodes 6,8.

The present disclosure discloses methods and systems for designing and operating amplifiers which can obtain neural response data during some or all of the period 402 by not imposing blanking throughout that entire period. Some embodiments may thus obtain neural response recordings during some or all of the stimulus itself. Some embodiments of the invention achieve this by injecting a compensating signal into the amplifier which partially or completely cancels out the stimulus artefact, or stimulus crosstalk, as seen on the recording electrode(s). In the embodiment of FIG. 3 this is effected by DAC 130. This cancellation reduces the dynamic range of the signal sufficiently that it can be amplified and digitised in a practical system. Further subtraction of the stimulus artefact may then be performed by controller 116 using digital signal processing techniques, if required.

Figure 5A:
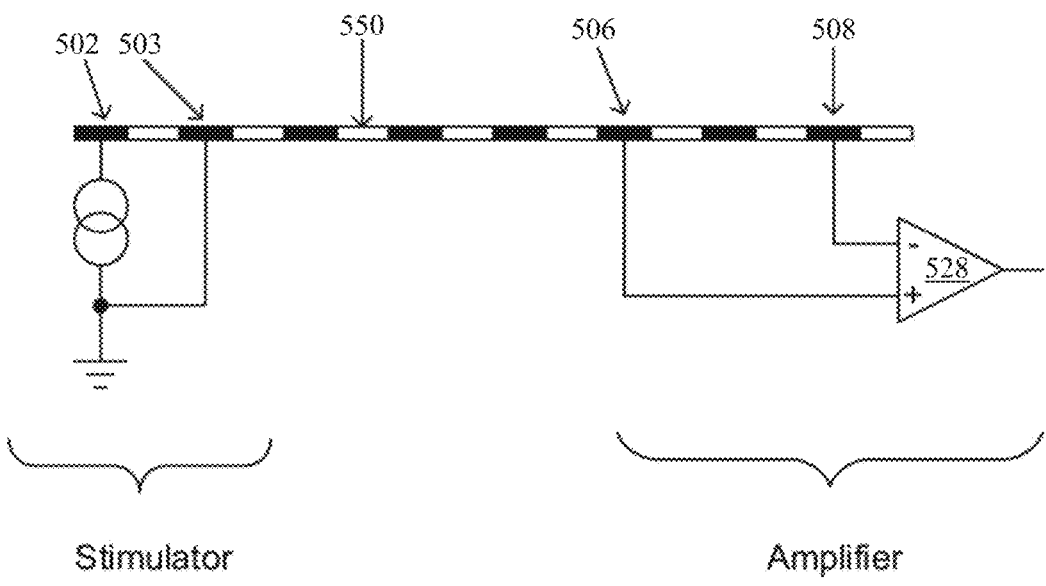
FIG. 5a depicts an example configuration of stimulation and recording electrodes for ECAP recording.

In order to explain the principles of such embodiments of the invention, we use a simple model to explain how the stimulus crosstalk voltages observed at the recording electrodes relate to the delivered stimulus. FIG. 5a depicts an example configuration of stimulation and recording electrodes for ECAP recording. This configuration utilises an implantable electrode array 550, stimulation electrodes 502, 503, an evoked response measurement electrode 506 and a measurement reference electrode 508. The patient's tissues, consisting of an ionic solution, are modelled by a resistor network, shown in FIG. 5b, which depicts an electrical model of the configuration of FIG. 5a. The electrode-tissue interface, which is a metal-electrolyte interface, is modelled by a set of constant-phase elements (CPEs) 502a, 503a, 506a and 508a. The model of FIG. 5b contains enough elements to reason about the invention, however the exact choice of model is not critical and additional or alternative modelling elements may be used such as elements of FIG. 3 and/or elements disclosed in the aforementioned PCT/AU2019/051160.

Figure 5B:
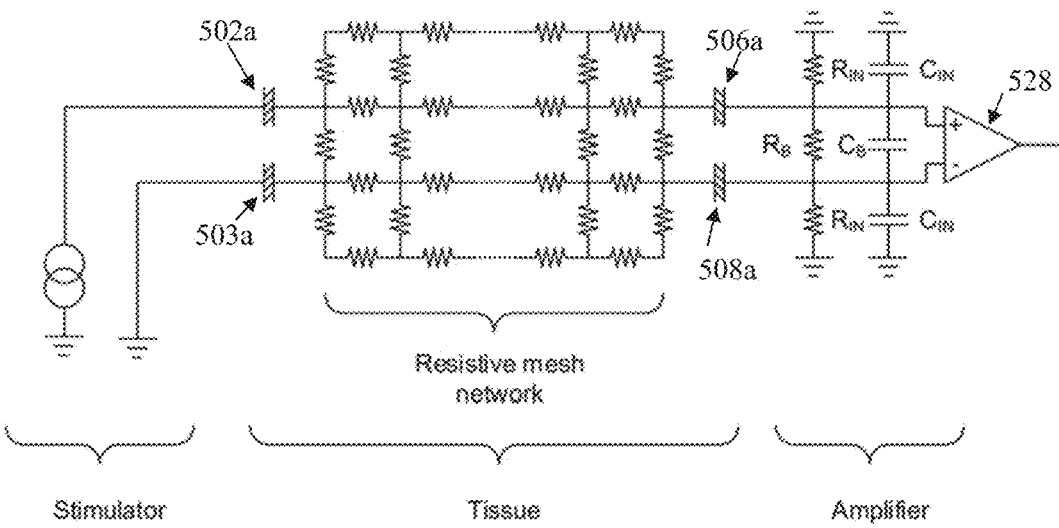

Salient behaviours of the model of FIG. 5b include the following. First, if no current flows through the recording electrodes 506, 508, the electrode-tissue interface will not develop a voltage during stimulus or recording, and so the voltage measured on the recording electrodes will be identical to that at the corresponding location in the resistor mesh. Second, if a constant current is driven between the stimulating electrodes 502, 503, then a respective constant voltage is developed at all locations in the resistor mesh, regardless of the respective voltage developed across each stimulating electrode's electrode-tissue interface, 502a, 503a. Thus when recording ECAPs the use of a high impedance amplifier 528 is beneficial in order to minimise current flowing through the recording electrodes 506, 508.

Combining the above-noted model behaviours, it can be seen that when a constant current is applied to the stimulus electrodes 502, 503, a constant crosstalk voltage appears at each recording electrode. Some embodiments of the present invention are based on the insight that this observation can be used to design amplifiers and/or ECAP measurement systems which calculate or estimate this constant crosstalk voltage during each stimulus phase, and then take steps to compensate for or remove the crosstalk voltage in the process of measurement. Such embodiments are referred to as undertaking "constant compensation". In constant compensation, the compensation signal takes on and retains a single value during each phase of the stimulus. The remainder of the compensation can be performed using a DSP (controller 116) after digitisation, as long as the constant compensation is sufficient to prevent the signal chain from clipping or otherwise losing information.

Further embodiments of the invention may additionally or alternatively provide for non-constant compensation, in order to cancel a non-constant stimulus crosstalk voltage arising upon the one or more sense electrodes as a result of delivery of the stimulus. By considering again the model of FIGS. 5a and 5b, or the like, it is possible to adapt some of the designs presented herein to handle a non-constant crosstalk voltage on the recording electrodes. Non-constant voltages would be expected, for example, in the following circumstances: (i) if the stimulus current were not constant, but varied during the stimulus pulse; (ii) if the stimulus were delivered in constant-voltage mode, or in some other manner not involving constant-current; (iii) if the recording electrode were also serving as a stimulating electrode, or otherwise was being used to carry current during the stimulus; and/or (iv) if stimulus artefact from other sources, such as charge accumulation upon electrodes as disclosed in the aforementioned PCT/AU2019/051160, were to cause an observable voltage to appear.

Therefore, in cases where non-constant stimulus crosstalk voltage arises in the measurement circuitry, the stimulus crosstalk cancellation signal could be configured to vary during the stimulus pulse in a corresponding manner as the stimulus crosstalk, so as to optimise stimulus crosstalk cancellation. The variation of the stimulus crosstalk cancellation signal could be controlled so as to be in accordance with measurements of stimulus crosstalk occurring in a previous stimulus or previous stimulus phase, and/or could be controlled in accordance with predictions made using a model. In non-constant compensation, the compensation signal may take on multiple values during each phase of the stimulus.

Figure 6:
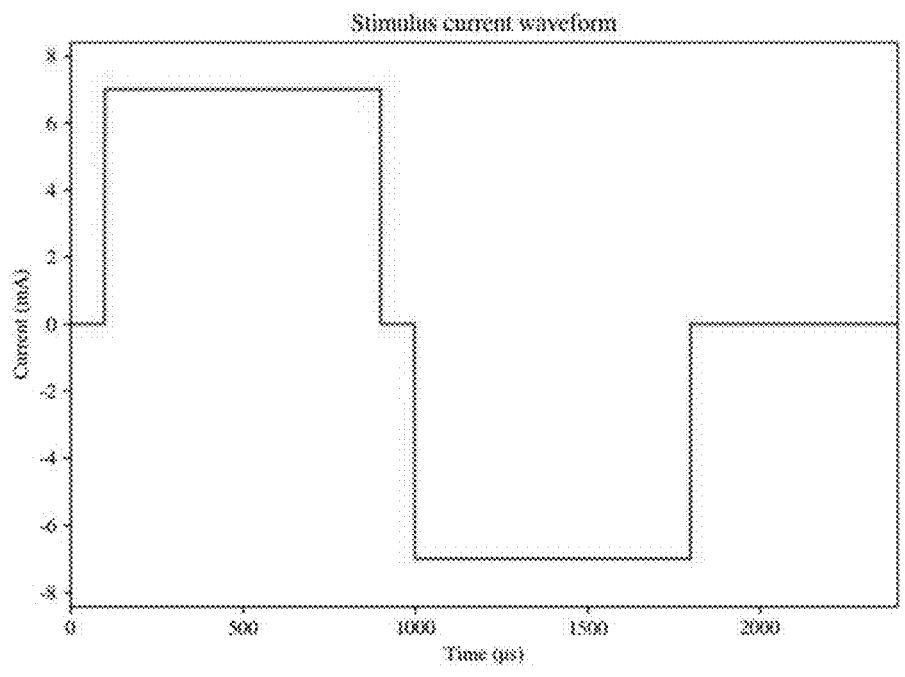
FIG. 6 depicts a biphasic stimulus waveform.

To further elucidate these and other embodiments of the invention, we introduce some example waveforms to show a compensating signal and its application. This example is deliberately chosen such that the compensating signal is not exactly the same as the electrode waveform, which is a result of the single-ended amplifier having different gains for the Rec input and Compensating input, respectively. This example provides a basic demonstration of crosstalk compensation. This models a basic ECAP recording configuration, similar to those encountered in SCS. An array of 12 electrodes is linearly arranged. The applied stimulus consists of a biphasic waveform, 7 mA amplitude, 800 μs pulse width, as depicted in FIG. 6. Stimulation is delivered between electrodes 1 ("stim") and 2 ("return"). The stimulation impedance is considered to be 1000 ohms, and the electrode-tissue interface is modelled with a 2 μF capacitance, similar to conditions encountered in SCS. The amplifier input impedance is assumed to be infinite.

Figure 7:
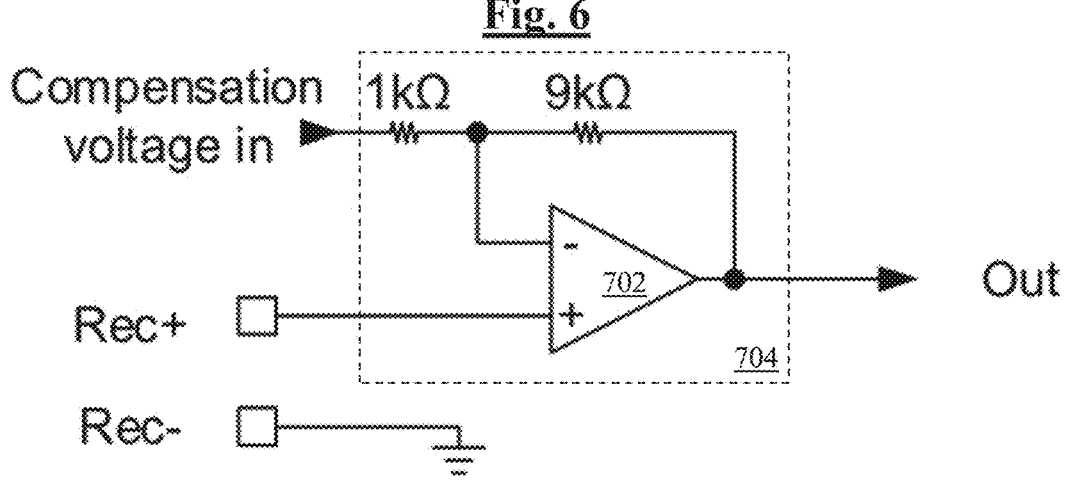
FIG. 7 depicts a measurement amplifier for making single-ended ECAP measurements with crosstalk compensation in accordance with an embodiment of the invention.

In this example, as shown in FIG. 7, a single-ended amplifier 702 is used. This is configured to provide a gain of 10, and has an input for a compensating signal in the form of a voltage. In this implementation, the gain from the recording electrode Rec+ input to the output is 10, and the gain from the compensating input to the output is −9. Thus, to compensate or cancel a stimulus crosstalk voltage X observed on the recording electrode Rec+ so as to obtain a zero output, a compensating signal of (10/9·X) must be applied to the compensation signal input.

Figure 8:
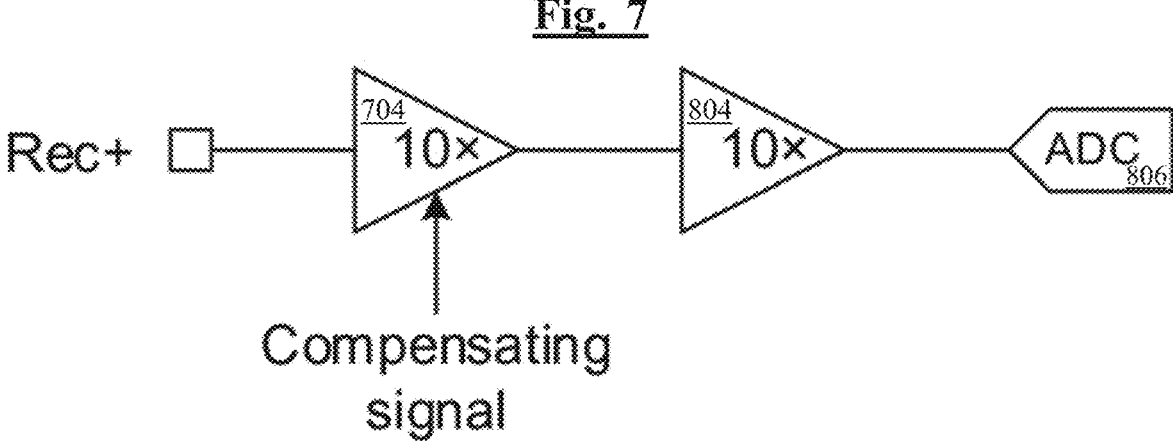
FIG. 8 illustrates the broader signal chain of the embodiments of FIGS. 6-7.

FIG. 8 further illustrates the broader signal chain of the example of FIGS. 6-7. As can be seen, the example system in which amplifier 702 is applied has a further gain stage 804 and an ADC 806 for acquiring ECAPs. To give a typical case, this ADC 806 has a maximum input range of ±1 V, and so the maximum uncompensated input range at the electrode Rec+ is ±10 mV, if clipping is to be avoided. The first-stage amplifier 702 output thus must be within the range ±100 mV to avoid clipping the downstream signal chain and losing ECAP information. Recalling that the stimulus electrodes' voltage during a stimulus is of the order of ±10 V, and that similar voltages are observed on nearby electrodes, it can be observed that stimulus crosstalk cancellation must achieve better than about 10/0.1, i.e. 40 dB, cancellation of stimulus crosstalk in order to avoid the measurement chain clipping during each stimulus phase. The required degree of stimulus crosstalk cancellation may differ in other embodiments depending on the particular patient's stimulus requirements and tissue conditions, as well as the amplifier chain in use.

To continue with the example of FIGS. 6-8, we consider two stimulation scenarios. In the first scenario, traditional "passive ground" stimulation is used, which we find requires non-constant crosstalk compensation within each stimulus phase. In the second scenario, a "virtual ground" stimulation mode is used, for example as disclosed in International Patent Publication No. WO 2014/071445, the contents of which are incorporated herein by reference. In this second scenario we find that constant crosstalk compensation can be applied in each stimulus phase, as explained further in the following.

Figure 9:
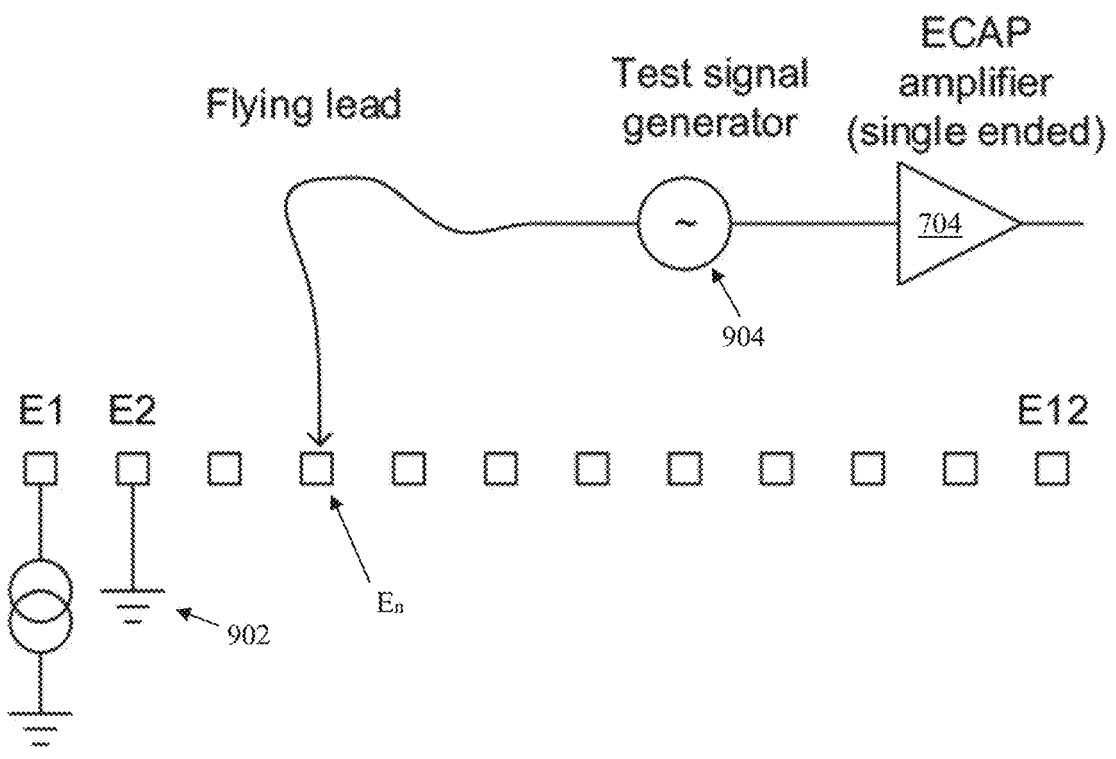
FIG. 9 illustrates an experimental configuration for crosstalk compensation with passive ground in accordance with an embodiment of the invention.

FIG. 9 illustrates the experimental configuration which includes an implantable lead electrode array, applying stimuli at electrodes E1 and E2 with a passive ground 902. Single ended recordings are made from a single recording electrode $E_n$ by amplifier 704. A sine wave source 904 simulates a biological signal which is superimposed over the observed stimulus crosstalk from the recording electrode. Source 904 simulates a biological signal by including a sine wave of 4 kHz, with 50 μV amplitude at the input of amplifier 704. This amplitude is representative of a relatively large ECAP observed in practical SCS recording situations. A flying lead allows for measurements to be made on different electrodes $E_n$.

Figure 10:
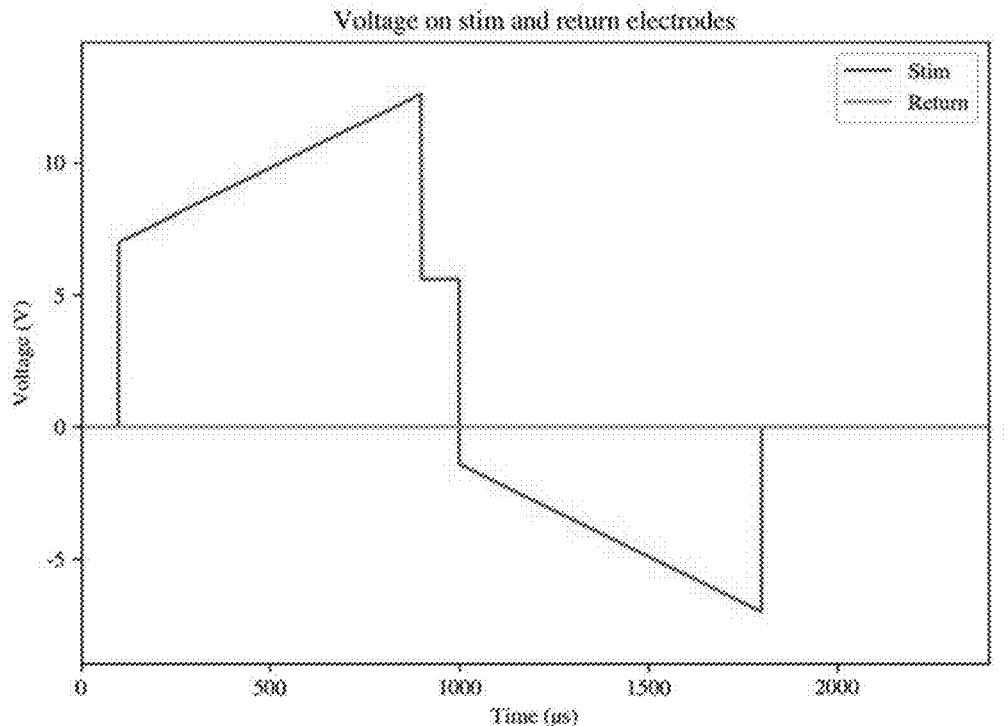
FIG. 10 is a plot of the voltages arising upon stimulus and return electrodes of FIG. 9 during application of a constant current stimulus.

FIG. 10 is a plot of the voltages arising upon the stimulus and return electrodes (E1 and E2) during application of the constant current stimulus of FIG. 6. During each phase of the stimulus the current between the stimulus and return electrodes sets up a voltage between the electrodes, and this voltage comprises two components. The resistive nature of the bath between the electrodes (as depicted in FIG. 5b) contributes a voltage component in FIG. 10 which is a constant multiple of the current. The capacitive nature of the metal-electrode electrolyte interfaces 502a and 503a is charged by the stimulus current, and contributes a linear ramp voltage component in FIG. 10. As can be seen large voltages of the order of 10 V arise on the stimulus electrode E1, whereas the return electrode E2 sees zero voltage as it is grounded.

Figure 11:
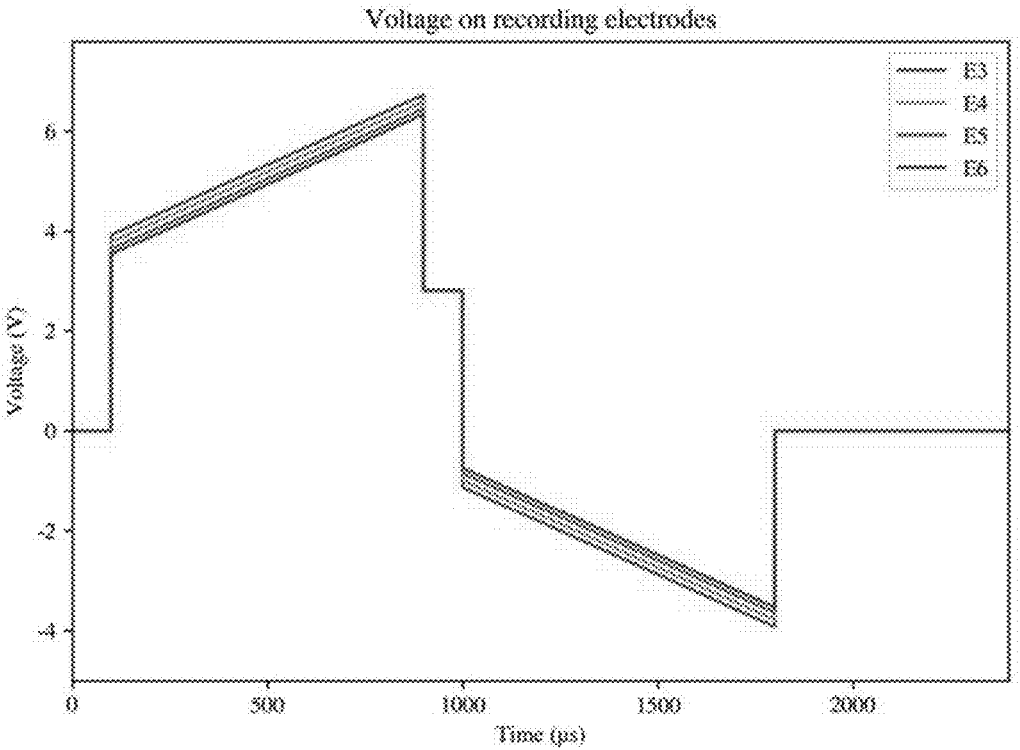
FIG. 11 is a plot of the voltages observed on recording electrodes of FIG. 9 during the stimulus.

FIG. 11 is a plot of the voltages observed on electrodes E3 to E6 during the stimulus. As can be seen the electrodes E3 to E6 experience a stimulus crosstalk voltage which reduces with increasing distance from the stimulus electrodes, but which in all cases is a significant fraction of the voltage seen on the stimulus electrode E1, reaching magnitudes as large as about +6 V and −4 V.

One of the stimulating electrodes is grounded, and so this acts as the reference for the recording amplifier 704. The voltages on the recording electrodes E3 to E6 seen in FIG. 11 all exceed the amplifier's uncompensated limit of ±10 mV by a large margin. Accordingly, a compensation signal must be applied if it is to be possible to record the neural response during the stimulus. The voltages on the recording electrodes seen in FIG. 11 are not constant during each phase, due to the use of a grounded return stimulation electrode as the reference, so a non-constant compensation must be used.

Figure 12:
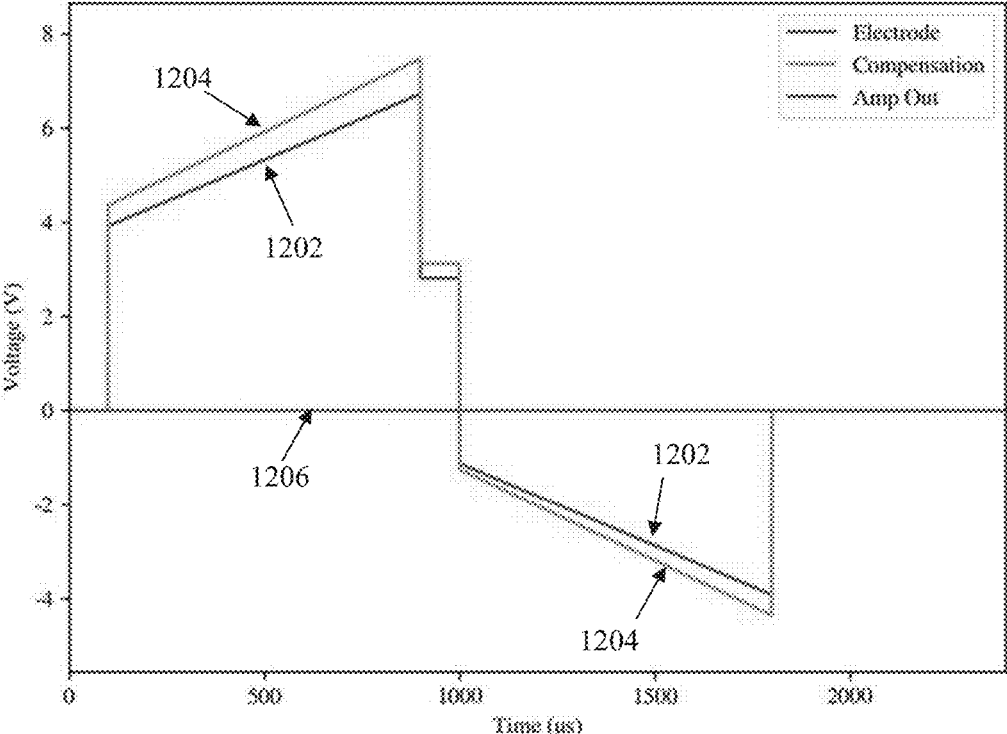
FIG. 12 illustrates electrode, compensation and amplifier output waveforms when making a single ended recording with crosstalk cancellation.
Figure 13:
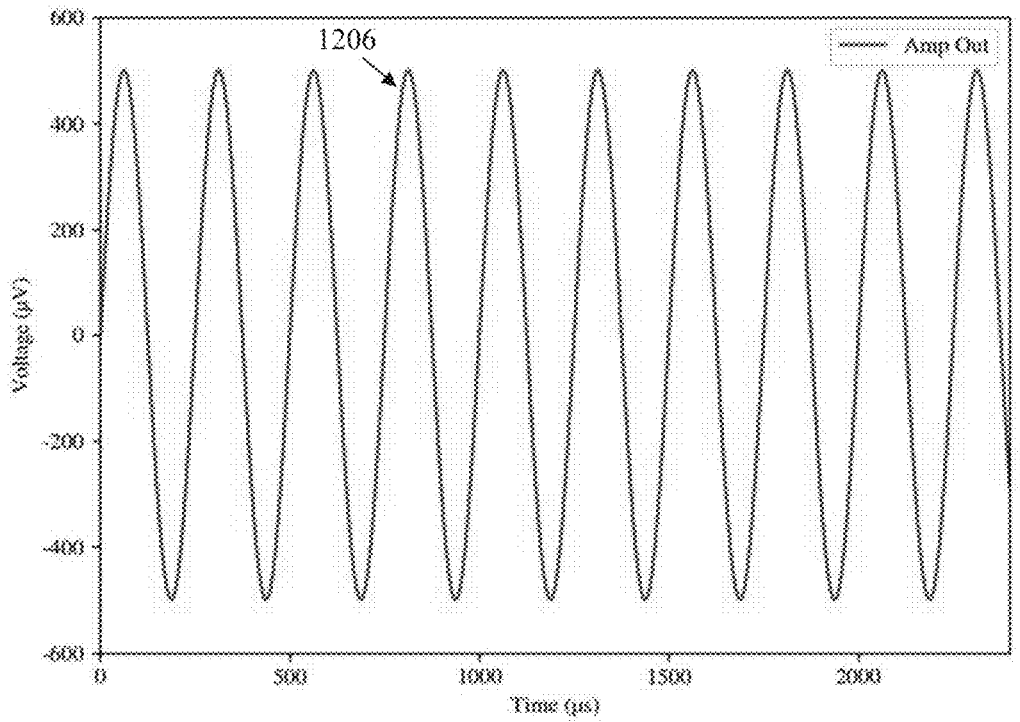
FIG. 13 is a detailed view of the amplifier output of FIG. 12.

FIG. 12 illustrates waveforms when making a single ended recording on E3 throughout a stimulus, while applying crosstalk cancellation. The E3 electrode voltage profile 1202 is the same as shown in FIG. 11. Knowing this profile, for example by recording 1202 during previous application of an identical stimulus, allows a suitable crosstalk cancellation signal profile 1204 to be determined. As discussed hereinbefore in relation to FIG. 7, signal 1204 can be calculated as being a 10/9 multiple of signal 1202. When the crosstalk cancellation signal 1204 is applied to measurement amplifier 704 as shown in FIG. 12, the amplifier output 1206 remains unaffected by stimulus crosstalk, as desired. In particular, as a result of compensation the amplifier output 1206 is well within the ±100 mV clipping limit. FIG. 13 is a detailed view of the amplifier output 1206 for this example, where crosstalk cancellation signal 1204 has been applied. As can be seen in FIG. 13, the 50 μV test signal from generator 904, with 10× gain, is clearly visible in the amplifier output, and the amplifier output 1206 is well within the ±100 mV clipping limit.

Signals on the stimulating electrodes can be estimated using the equations of the voltage on a CPE. For a simple CPE (without series resistance) and a fixed current the voltage can be estimated using the equation:

$$V = I\left(R + \frac{1}{C_0}t^\alpha\right)$$

where I is the current, $C_0$ is the pseudo-capacitance of the electrode, t is time and α is the pole fraction for the CPE.

Figure 14:
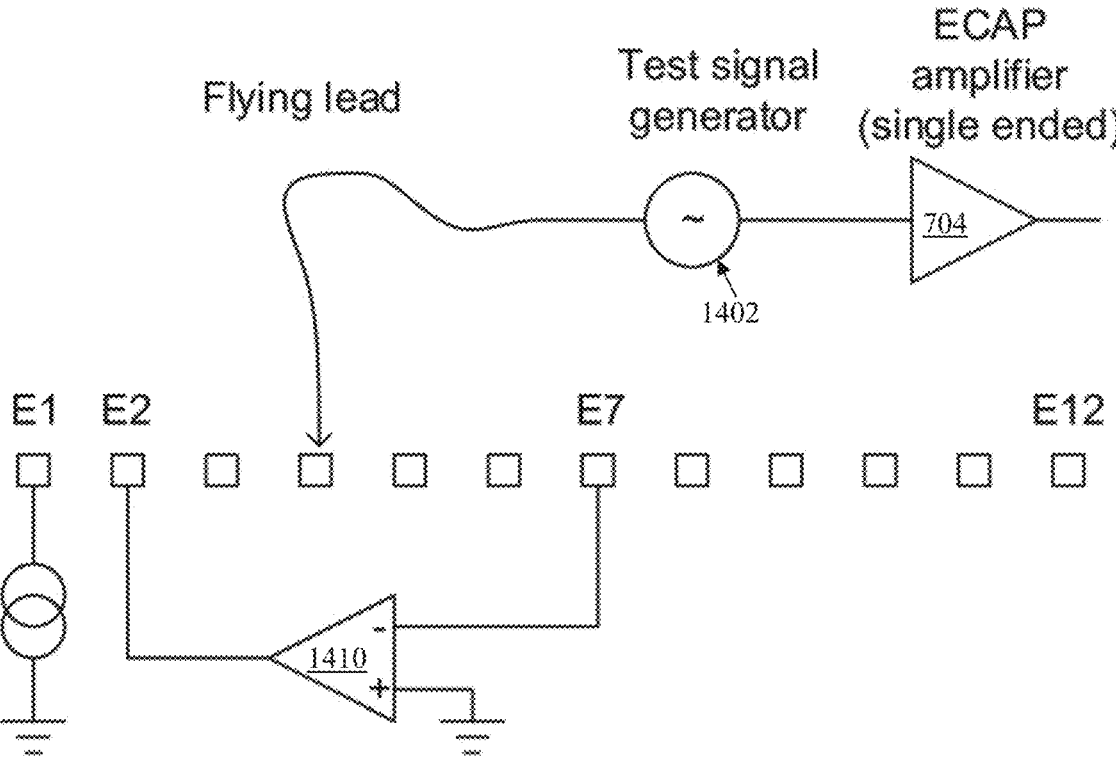
FIG. 14 illustrates the experimental configuration for crosstalk compensation with virtual ground in accordance with another embodiment of the invention.

As noted above the example of FIGS. 5-13 involves the stimulus return electrode 503 (or E2) being connected directly to ground 902. We now turn to another example, instead involving the use of virtual ground, as described in the aforementioned WO 2014/071445. FIG. 14 illustrates the experimental configuration of an implantable lead for a virtual ground recording. A sine wave source 1402 once again simulates a biological signal which is superimposed onto a stimulus crosstalk signal experienced by the recording electrode. A flying lead allows for measurements to be made on different electrodes.

As described more fully in the aforementioned WO 2014/071445, the virtual ground amplifier 1410 actively drives the return electrode E2 such that the common-mode voltage observed by the recording electrodes is, or is close to, zero. This ensures that the time-varying voltage component across the electrode-tissue interfaces at the stim and return electrodes E1 and E2 is not impressed on the recording electrode, allowing constant compensation to be used in this embodiment.

Figure 15:
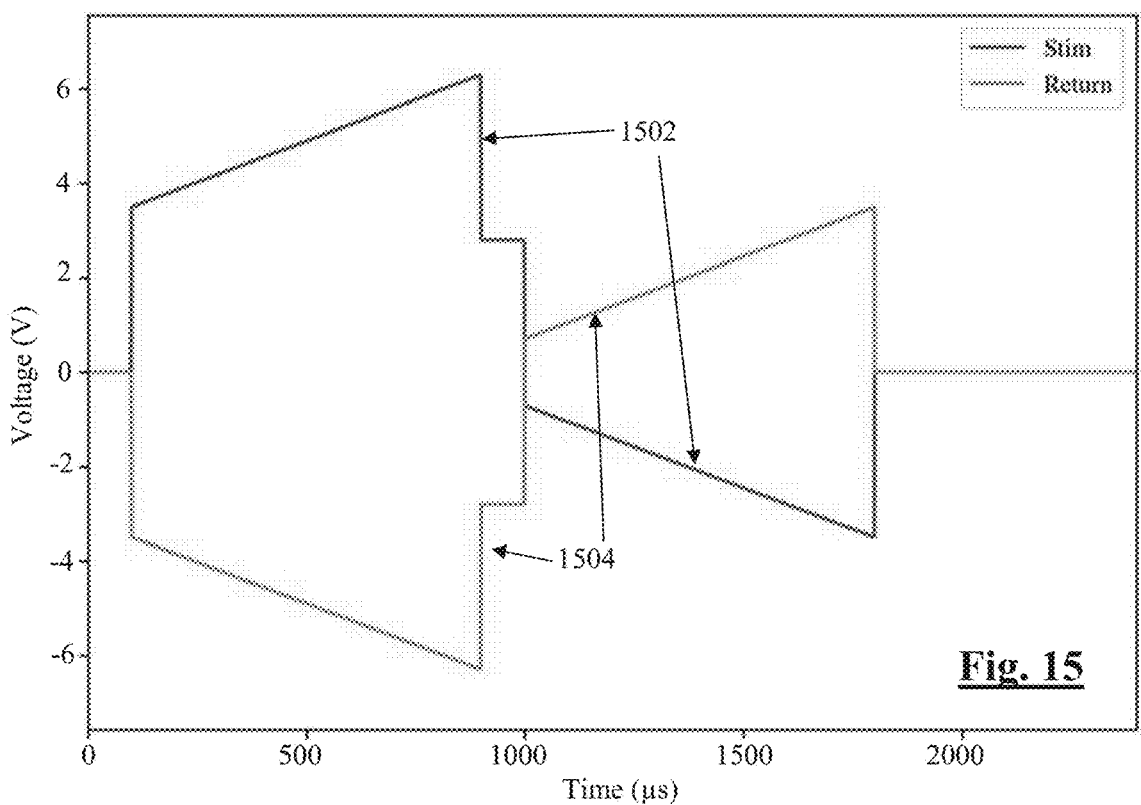
FIG. 15 is a plot of the voltages arising upon stimulus and return electrodes of FIG. 14 during application of a constant current stimulus.

FIG. 15 illustrates the resulting voltage 1502 on the stim electrode (E1) and the resulting voltage 1504 on the return electrode (E2) in the embodiment of FIG. 14, when the stimulus of FIG. 6 is applied. As can be seen the return electrode voltage 1504 is no longer held to zero by a ground connection, but instead due to the operation of the virtual ground amplifier 1410 the return electrode voltage 1504 takes an inverse profile to the stimulus electrode voltage 1502.

Figure 16:
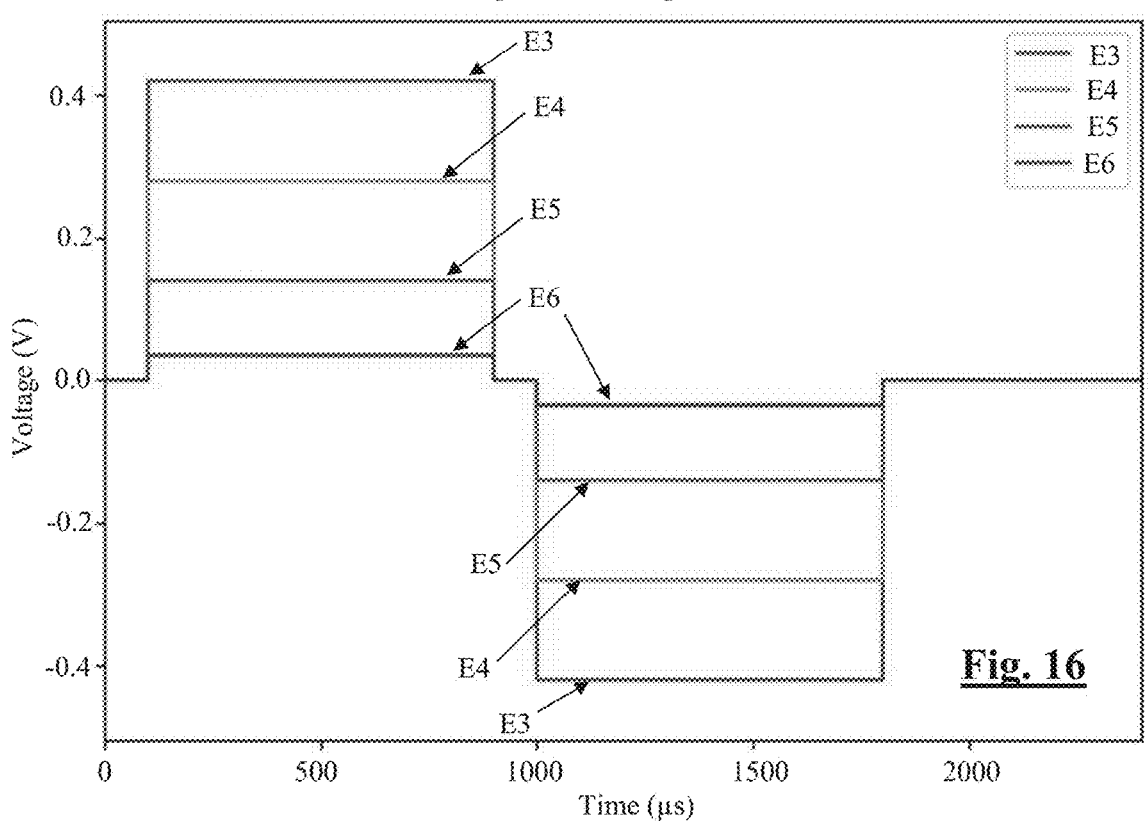
FIG. 16 is a plot of the voltages observed on recording electrodes of FIG. 14 during the stimulus.

FIG. 16 is a plot of the voltages observed on the recording electrodes E3-E6, during application of the stimulus of FIG. 6 to the embodiment of FIG. 14. With increasing distance from the stimulus electrodes, less stimulus crosstalk is experienced at the respective recording electrode. Further, by comparison to FIG. 11 it can be seen that less crosstalk is suffered in the present embodiment as compared to the embodiment of FIGS. 5-13. Nevertheless, the stimulus crosstalk voltages experienced on the recording electrodes all exceed the amplifier's uncompensated limit of ±10 mV. Accordingly, a crosstalk cancellation signal, or compensation signal, must be applied in order for it to be possible to record neural activity during the stimulus without amplifier saturation.

Figure 17:
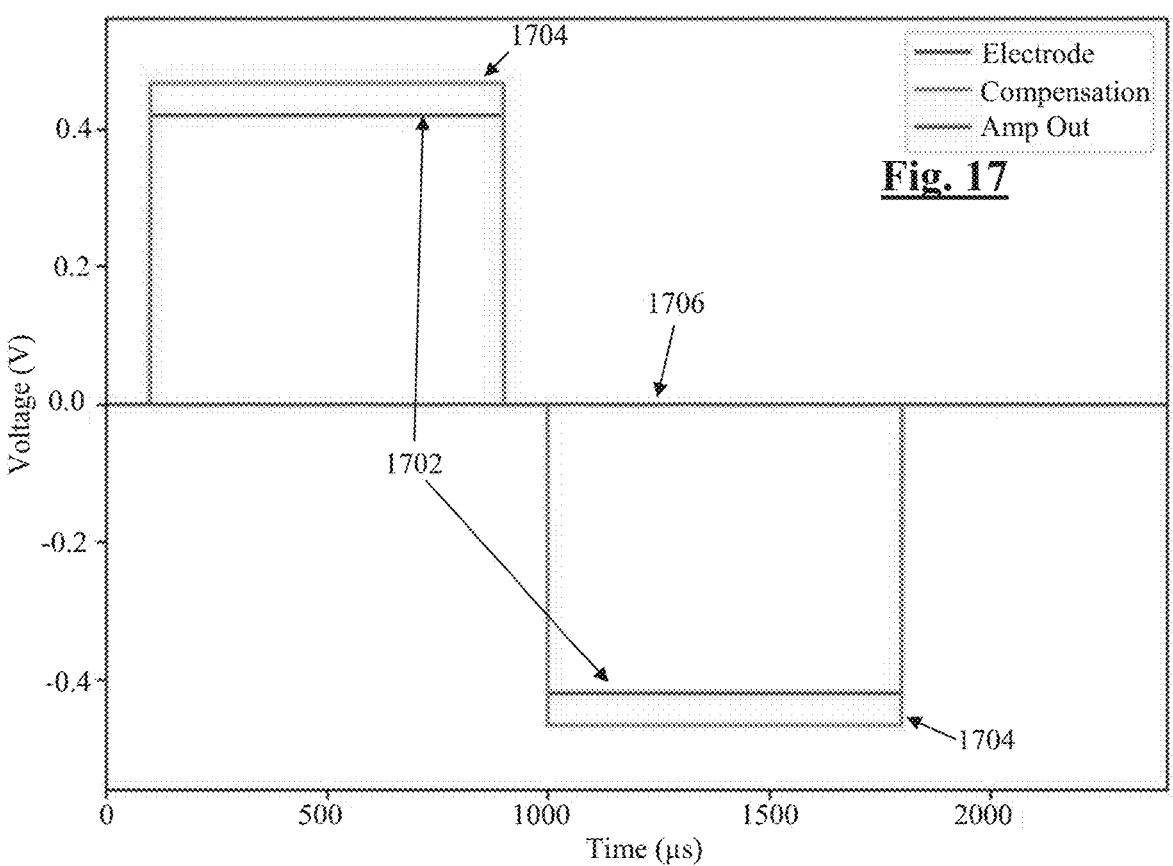
FIG. 17 illustrates electrode, compensation and amplifier output waveforms for the embodiment of FIG. 14 when making a single ended recording with crosstalk cancellation.
Figure 18:
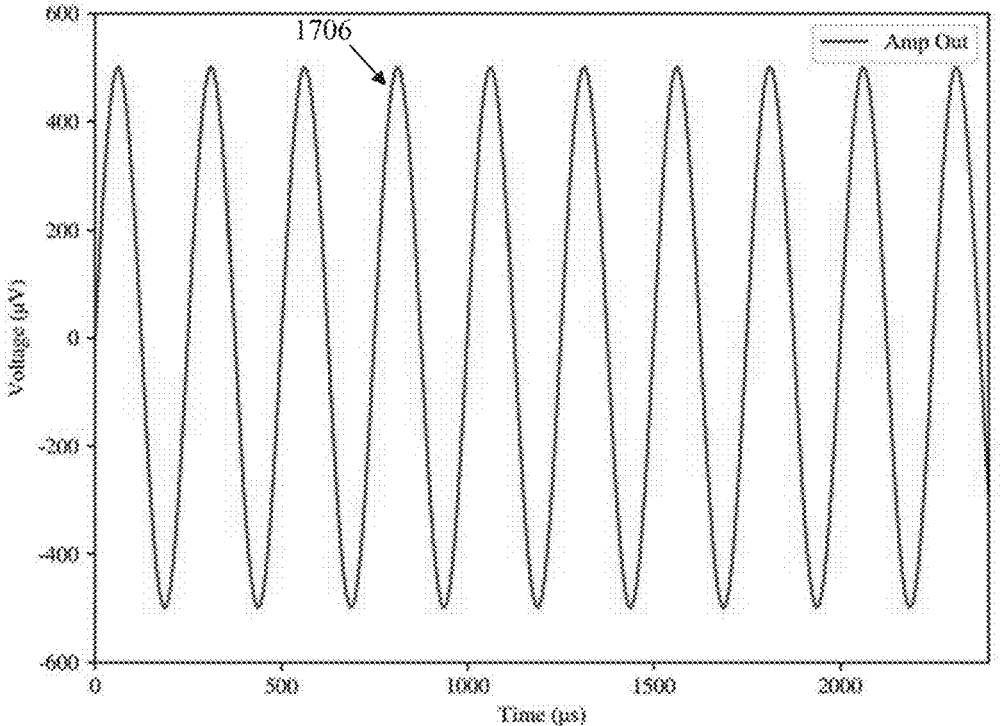
FIG. 18 is a detailed view of the amplifier output of FIG. 17.

FIG. 17 is a plot of the stimulus crosstalk voltage 1702 experienced on recording electrode E3. FIG. 17 further plots a suitable crosstalk cancellation signal 1704, which is determined as being a multiple of 10/9 of 1702. Also shown is the resulting output 1706 produced by amplifier 704 as a result of application of such constant compensation on E3. After this compensation, the amplifier output 1706 remains well within the ±100 mV limit. FIG. 18 provides a detailed view of amplifier output 1706. The 50 µV test signal, with 10× gain, is clearly visible in the amplifier output 1706.

In light of the above-described embodiments, further embodiments of the invention are also described in the following. These embodiments generally seek to provide: (i) an ECAP amplifier or amplifier chain, whose purpose is to produce a useful representation of an ECAP during and/or after a stimulus; (ii) a means for injecting a compensating signal into the amplifier or amplifier chain, in order to partially or wholly cancel a stimulus crosstalk voltage observed at the recording electrodes; and (iii) a means for determining an appropriate compensating signal which best cancels stimulus crosstalk in the output of the ECAP amplifier. In some embodiments, these elements are combined into a single unit.

One element which may differ in alternative embodiments of the invention is the amplifier or amplifier chain. There are two basic categories of amplifier which can be used: single-ended amplifiers which record a potential from a single recording electrode with respect to a system ground, and differential amplifiers which record the potential between two recording electrodes, ignoring their common-mode signal relative to ground. In ECAP recording, we consider one electrode to be acting as the "reference" electrode, against which potentials are measured. Then, ECAPs can be measured on the other electrodes with respect to that electrode. Multiple amplifiers can also be combined, for example by placing multiple amplifiers in series for increased gain. In these cases, the categories can be mixed, eg. a differential amplifier stage may be followed by a single-ended amplifier stage.

Single-ended amplifiers measure their input voltage with respect to a system ground. In ECAP recording, this typically means connecting the measurement reference electrode to the recording system ground during a measurement period. When measuring during a stimulus, however, this is more complicated: some stimulation modes involve connecting one of the stimulus electrodes to ground, or to another fixed potential. To avoid unintended current flow during stimulation, none of the recording electrodes should then be connected to a fixed potential. The fixed-potential stimulus electrode then acts as the reference electrode during recording.

If a stimulus electrode is used as the reference, the potential difference between the reference and measurement electrodes will include the voltage across the electrode-tissue interface, because a significant current flows through the stimulating electrodes. This may require non-constant compensation in order to maintain the signal within a suitable range for the measurement signal chain. This can be avoided by using other stimulus modes: for example, virtual ground. In those cases, the electrode-tissue voltages from the stimulus electrodes can be excluded, and constant compensation can be used.

In contrast, differential amplifiers measure their input voltage between two electrodes. These are more complicated than single-ended amplifiers, but have the advantage that they reject common-mode signals; thus virtual ground is not required.

The described embodiments herein recognise that there are many ways to apply stimulus crosstalk cancellation in order to compensate a measurement amplifier. Some further examples are described in the following.

In general, it is desirable to maintain a high input impedance to the recording electrode, to avoid driving a voltage across the electrode-electrolyte interface. However, it may be acceptable for current to flow during non-recording periods, such as while the compensating signal is being adjusted, as long as it is held constant during the periods when the ECAP is being recorded, so that a constant voltage is maintained during those times.

It is desirable for the circuit to be able to compensate the largest expected crosstalk voltage. As shown in one example in FIG. 11, the crosstalk voltage can be as high as the stimulus voltage, depending on the physical arrangement of stimulus and recording electrodes.

Some of the following examples are standalone circuits which do not have voltage gain, and which can be placed in front of any suitable ECAP amplifier or amplifier chain in order to extract a suitable ECAP recording. Some other examples are modifications to an amplifier to provide compensation and gain at the same time.

Some examples provide for a feedback network voltage injection in order to effect stimulus crosstalk cancellation. Given a voltage source, this method applies a voltage to some point in the amplifier's feedback network, which adjusts the output by an offset defined by the applied voltage. In these examples, a digital to analog converter (DAC) is shown as the compensating source, whereby a digital signal processor (DSP) (e.g. controller 116) can be tasked with controlling the DAC appropriately. Alternatively the voltage to be injected could be sourced from an analog circuit for example.

Figure 19:
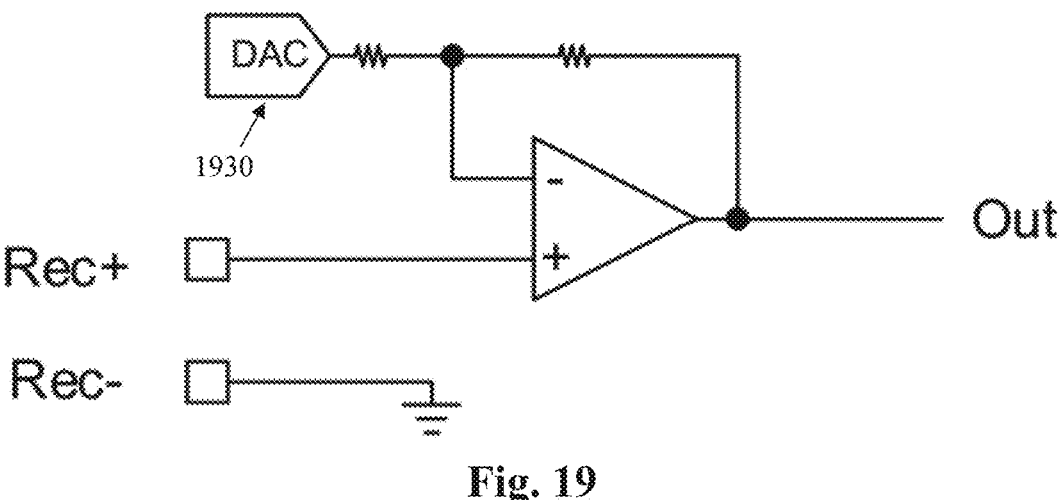
FIG. 19 depicts a measurement amplifier for making single-ended ECAP measurements with crosstalk compensation in accordance with a further embodiment of the invention.

FIG. 19 is an alternative to the embodiment of FIG. 7, in which a DAC 1930 is used to provide the stimulus crosstalk cancellation voltage. The resistances in the resistive chain between the DAC 1930 and the output amplifier may be set to any suitable values to give desired gain and desired operational ranges for the control voltage from DAC 1930.

Figure 20:
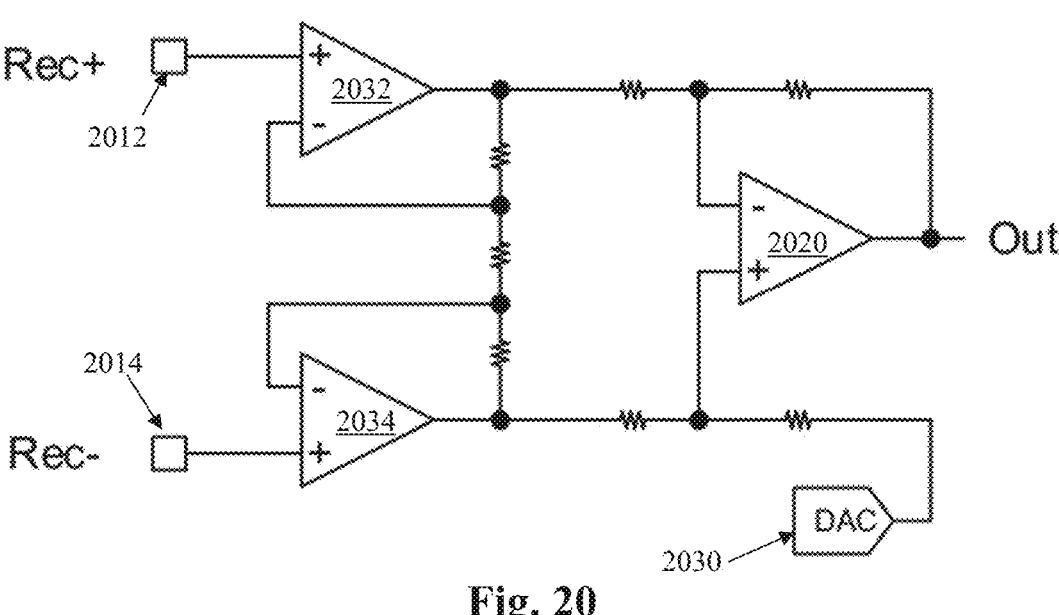
FIG. 20 depicts measurement circuitry for making differential ECAP measurements with crosstalk compensation in accordance with yet another embodiment of the invention.

FIG. 20 illustrates yet another embodiment of the invention, utilising differential recording from two recording electrodes 2012, 2014. A differential amplifier 2020, equipped with input buffer amplifiers 2032 and 2034 arranged to provide high input impedance and improved common-mode rejection ratio, outputs a signal indicating the difference in voltage arising between the recording electrodes 2012 and 2014. Stimulus crosstalk cancellation is effected by providing DAC 2030, which is positioned in the location shown in place of a ground connection. DSP controller 116 controls the DAC 2030 in a corresponding manner as described above in relation to the embodiments of FIGS. 5-18.

Further embodiments of the invention may additionally or alternatively provide for stimulus crosstalk cancellation to be effected by feedback network current injection, in addition to or as an alternative to voltage injection.

Figures 21, 22:
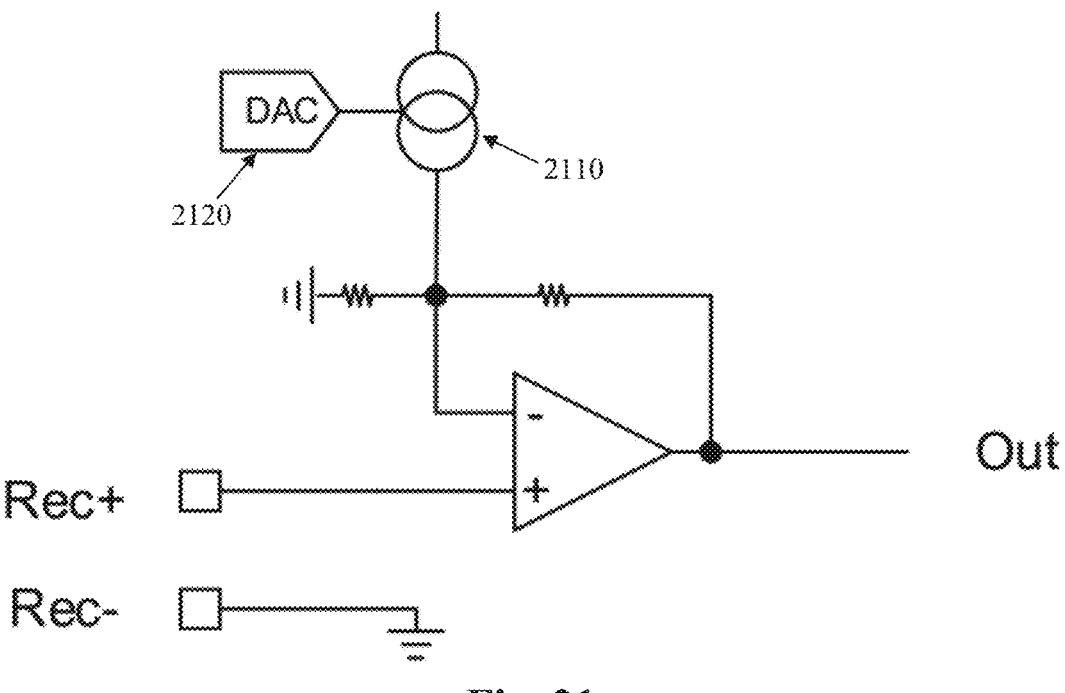
FIG. 21 depicts measurement circuitry for making single-ended ECAP measurements with crosstalk compensation in accordance with still a further embodiment of the invention.
FIG. 22 depicts measurement circuitry for making differential ECAP measurements with crosstalk compensation in accordance with still another embodiment of the invention.

FIG. 21 illustrates an embodiment providing single-ended recording and current injection for stimulus crosstalk cancellation. Elements in common with the embodiment of FIG. 7 function similarly and are not described again here. Current source 2110, under the control of DAC 2120, provides current to the midpoint of the resistive chain in the amplifier's feedback network, which adjusts the output by a constant offset so as to compensate for stimulus crosstalk experienced on the Rec+ electrode.

FIG. 22 illustrates an embodiment providing single-ended recording and current injection for stimulus crosstalk cancellation. Elements in common with the embodiment of FIG. 20 function similarly and are not described again here. Current source 2210, under the control of DAC 2220, provides current to the node at the measurement amplifier's inverting input, which adjusts the output by a constant offset so as to compensate for stimulus crosstalk experienced on the Rec+ electrode.

In the embodiments of FIGS. 21 and 22 a DAC is shown as the compensating source, however in other embodiments suitable control signals may be derived from other sources such as an analog circuit.

Figure 23:
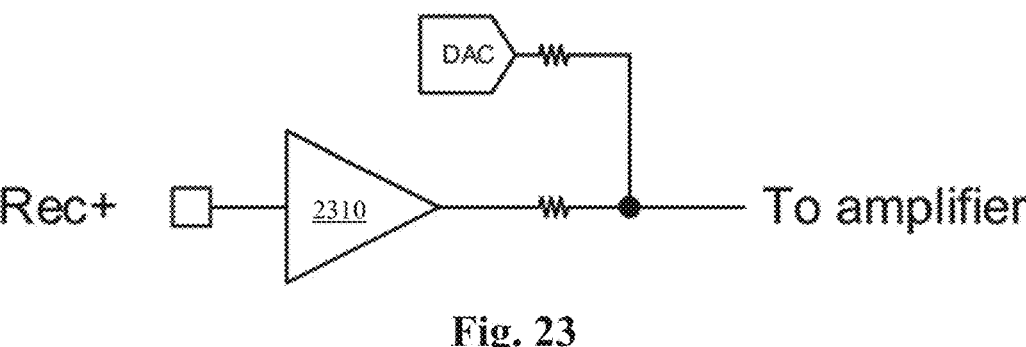
FIG. 23 depicts front-end mixing circuitry for making ECAP measurements with crosstalk compensation in accordance with an embodiment of the invention.

Further embodiments of the invention may additionally or alternatively provide for stimulus crosstalk cancellation to be effected by front end mixing. One such embodiment is shown in FIG. 23, which depicts compensation by using a voltage and summing circuit. This method uses a buffer 2310 and summing circuit comprising a DAC input and resistors, to adjust the input signal from the Rec+ electrode by an offset, while maintaining high impedance. The output of this summing circuit can be fed to a subsequent ECAP amplifier, whether single-ended or differential. The buffer 2310 ensures that the input impedance remains high, minimising current flow through the recording electrode's metal-electrolyte interface. Optionally, the buffer 2310 may have gain.

Again, while a voltage mode signal is used in FIG. 23, a current mode signal can be used in alternative embodiments in which stimulus crosstalk cancellation is effected by front end mixing.

A mixing approach can also be used to inject a compensating signal between multiple stages of an amplifier, rather than at the front end of the amplifier chain. As long as the preceding stages can handle the expected crosstalk voltages without clipping, this provides a great deal of flexibility in amplifier design.

Embodiments of the present invention can also differ in terms of the manner in which the stimulus crosstalk cancellation signal is determined. The stimulus crosstalk voltage arising on the recording electrode(s) depends primarily on the resistive coupling between all of the electrodes. In neuromodulation, this coupling can vary, for example in SCS as the patient moves about: their spinal cord moves inside the dura, displacing highly-conductive CSF with lower-conductivity neural tissue. Consequently, the stimulus crosstalk arising on the recording electrode(s) is expected to change over time.

The compensation signal can be determined by measuring the actual crosstalk voltage during the stimulus. This has the disadvantage that there is some period between the start of stim and the compensation signal reaching an appropriate value, meaning that part of the ECAP is lost. An alternative approach is to predict the crosstalk voltage in advance of the stimulus, and when applying a new stimulus to apply a compensation signal at the appropriate time relative to the new stimulus.

Combinations of the two methods can be used. For example, in a stimulus consisting of multiple phases, the crosstalk voltage can be measured during the first phase. The crosstalk voltage of the subsequent phases can then be predicted from this measurement, as the inter-electrode coupling would not change significantly during one stimulus (typically <1 msec).

Figure 24A:
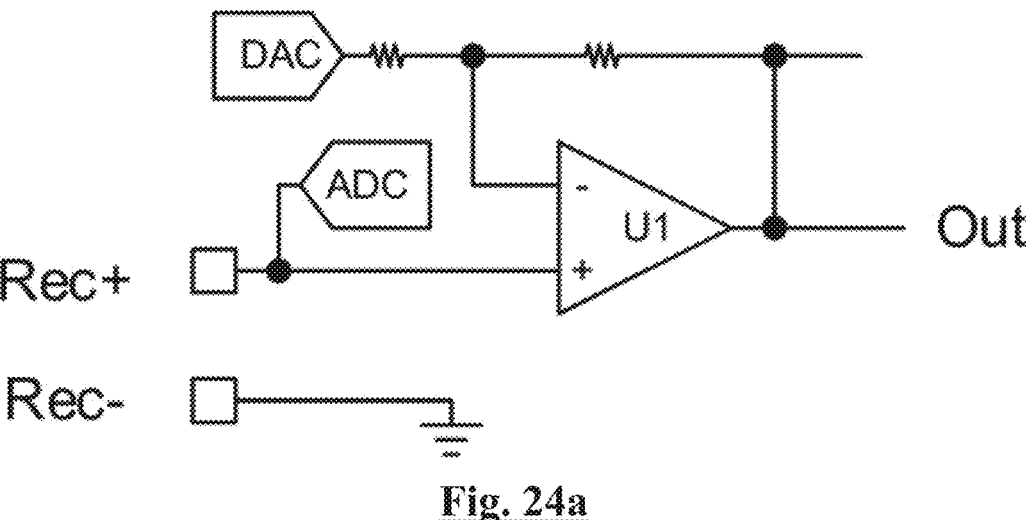
FIGS. 24a and 24b depict another embodiment for making single-ended ECAP measurements with crosstalk compensation.

In some embodiments, an approach to formulating the crosstalk cancellation signal is to measure the crosstalk voltage at the recording electrode(s) using an ADC, and to then immediately apply the appropriate compensating voltage using a DAC. FIG. 24*a* illustrates one such embodiment. The ADC and DAC need not have high resolution, only enough to keep the amplifier from clipping. The DAC noise is important, however, as it will add noise to the amplifier output.

Figure 24B:
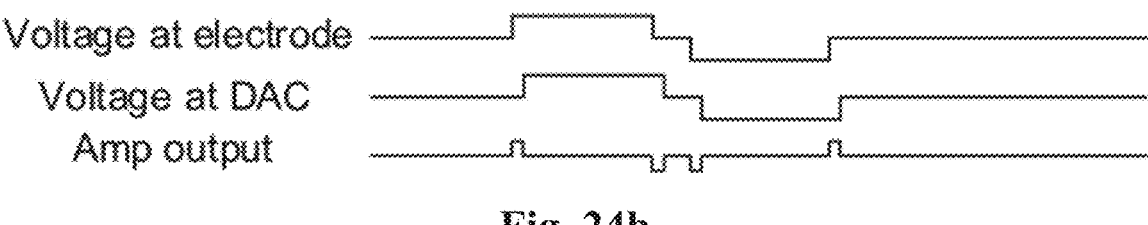

FIG. 24*b* depicts waveforms arising in the embodiment of FIG. 24*a* when compensating a single-ended amplifier using an ADC and DAC. In this scheme, the ADC is used to measure the new electrode voltage whenever it has changed, i.e. after every change in the stimulus current. This is used to calculate the correct DAC voltage to compensate for this electrode voltage. There is necessarily a delay between the change in electrode voltage and the consequent settling of the amplifier with a suitable compensation voltage. During these measurement and settling times, the amplifier output may exhibit large transients, and recording may be impossible. Accordingly, the measurement chain may be blanked briefly around the time of stimulus transients.

The method of FIG. 24 is for constant compensation, as seen by the voltages in FIG. 24*b*. However, this method is also amenable to non-constant compensation; the non-constant crosstalk voltage can be measured at one or at multiple points, and an appropriate compensation waveform driven to the DAC.

Figures 25A, 25B, 26:
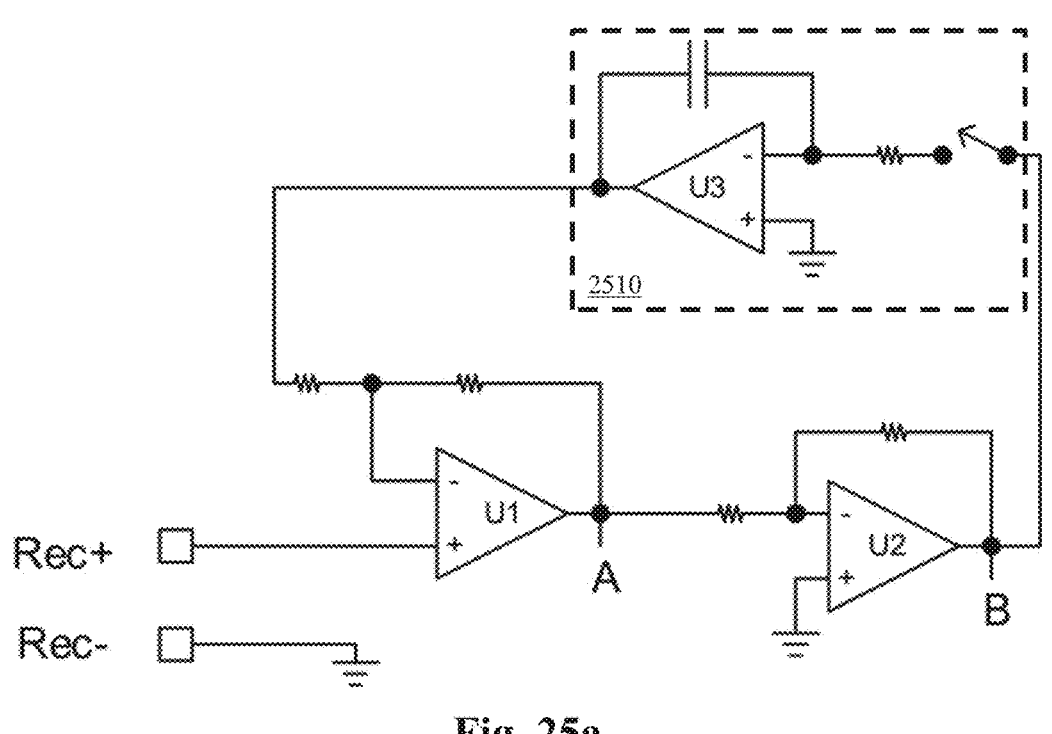
FIGS. 25a and 25b depict yet another embodiment for making single-ended ECAP measurements with crosstalk compensation.
FIG. 26 depicts front-end mixing circuitry for making ECAP measurements with crosstalk compensation in accordance with a further embodiment of the invention.

FIG. 25*a* illustrates yet another alternative embodiment, in which an analog approach is applied so as to use an error integrator 2510 to zero the output of some part of the signal chain. In this example, the compensating signal is stored on the integrating capacitor. In FIG. 25*a* U1 provides the first gain stage. This is configured as a non-inverting amplifier as for the embodiment of FIG. 7, in order to present a high input impedance to the recording electrodes, and allowing a compensating signal to be injected via the feedback network 2510. U2 provides an inverting function, and can be used as another gain stage. U3 is used to determine the compensating signal. When the switch in the integrator 2510 is closed, a feedback loop is formed, which adjusts the compensating signal such that the output of U2 is driven to zero. When the switch is opened, the value of the compensating signal thus determined remains held in the capacitor around U3. The output of U2 then reproduces any ECAP signal at the recording electrode.

FIG. 25*b* illustrates the signals in the embodiment of FIG. 25*a*, comprising a single-ended amplifier using an error integrator. In use, the switch would be closed in such a system before or during an anticipated change in the recording electrode voltage. The switch would be held closed until the compensation signal had attained the desired value. During the transitions where the new compensation signal is being determined, the amplifier output can swing significantly, but this contains no ECAP information. Thus this measurement period should be kept short. This could be done using a fixed time, or by measuring the amplifier output to determine when an acceptable level of compensation has been achieved, eg. the amplifier is sufficiently far from clipping. Once the compensation signal has settled, the switch is opened, and ECAP recording can be performed.

This particular embodiment has the advantage that it also cancels amplifier offset, and the inverting amplifier can provide further gain. Signals from point A or B may be fed to further amplifiers, or directly to an ADC to serve as the ECAP recording.

FIG. 26 illustrates another embodiment utilising an analog method, which uses a buffer, series capacitor, and switch. During and immediately after a change in the stimulus (e.g. the start or end of a stimulus phase), the switch is closed. After a certain time, allowing the capacitor to charge or discharge, the switch is opened and recording commences. The compensation signal is the voltage stored on the capacitor, which is added to or subtracted from the input voltage. In FIG. 26 the buffer may have voltage gain, at the cost of reducing the common-mode input range. This circuit may be used with either single-ended or differential amplifiers. It may be used to buffer and distribute one reference electrode to multiple differential amplifiers.

Figure 27:
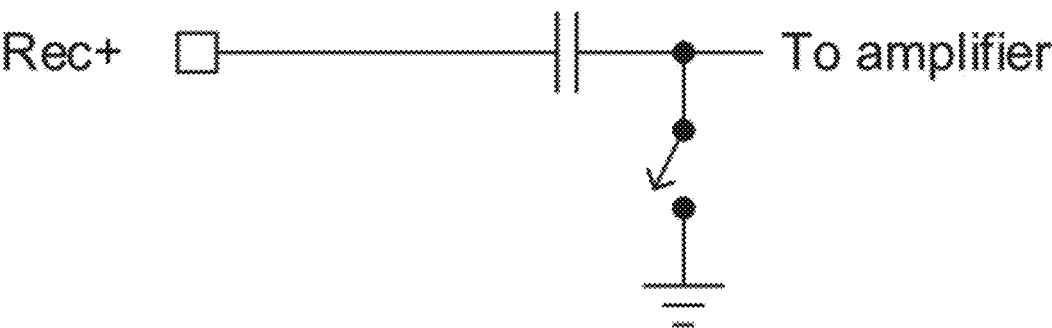
FIG. 27 depicts front-end mixing circuitry for making ECAP measurements with crosstalk compensation in accordance with still a further embodiment of the invention.

FIG. 27 illustrates yet another embodiment. This differs from FIG. 26 in that the buffer is omitted. The embodiment of FIG. 27 recognises that the buffer of FIG. 26 is optional if the downstream amplifier has high input impedance, because then significant current will only flow when the zeroing switch is closed, during which time recording is not possible anyway. When the switch is open, no current flows through the recording electrode, and its voltage remains constant. In this case, the compensating charge is stored on both the capacitor and at the metal-electrolyte interface. The impedance of the switch may be controlled to limit the current through the electrode to avoid unintended stimulation.

Embodiments of the present invention can also differ in terms of the manner in which the stimulus crosstalk cancellation signal is determined, by making predictions of crosstalk instead of or in addition to measuring crosstalk. These embodiments recognise that a neuromodulation device has a number of sources of information available, from which it is possible to predict the crosstalk voltage. For example, if the device changes the delivered stimulus current amplitude, the crosstalk voltage is expected to change accordingly. Also, measurements of crosstalk voltages on each stimulus can be used to predict future crosstalk voltages. For example, a predictor might estimate that the next stimulus will have the same crosstalk as the last, or that the crosstalk will continue to change at a constant rate observed previously.

Figure 28:
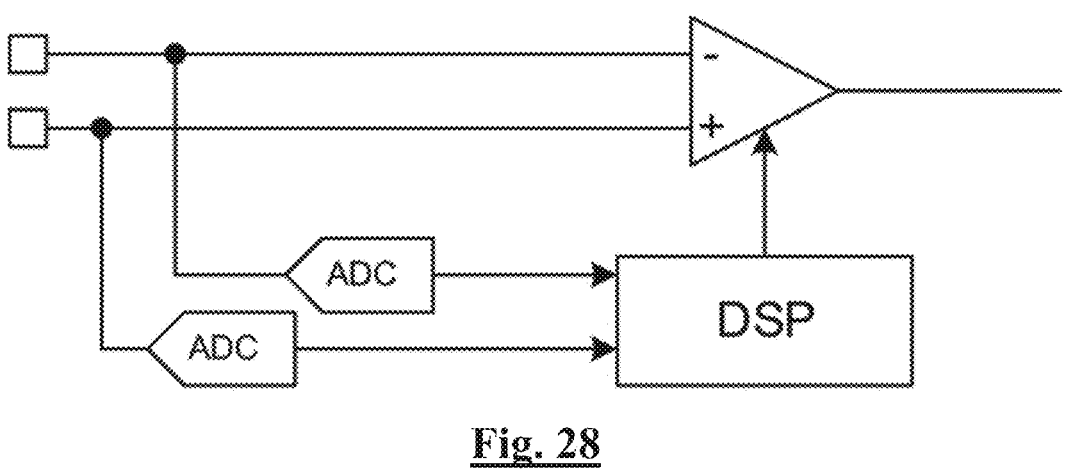
FIG. 28 depicts measurement circuitry for making differential ECAP measurements with crosstalk compensation in accordance with another embodiment of the invention.

In such embodiments stimulus crosstalk can be measured using dedicated ADCs, as shown in the embodiment of FIG. 28, in which stimulus crosstalk is measured directly at the electrodes and a compensation signal is calculated in the DSP. Within the DSP some aspect(s) of the signal are predicted in advance, thus minimising or eliminating the loss of ECAP signal during the measurement and settling time. In this embodiment we take one measurement at the start of the first phase of a multiphase stimulus to estimate the crosstalk transimpedance, and then predict what the crosstalk compensation signal should be for subsequent phases, based on this transimpedance and the relative currents of each phase. Another option which may be utilised is to take one measurement at the start of a stimulus phase, and then apply a non-constant compensation waveform scaled according to this measurement.

Figure 29:
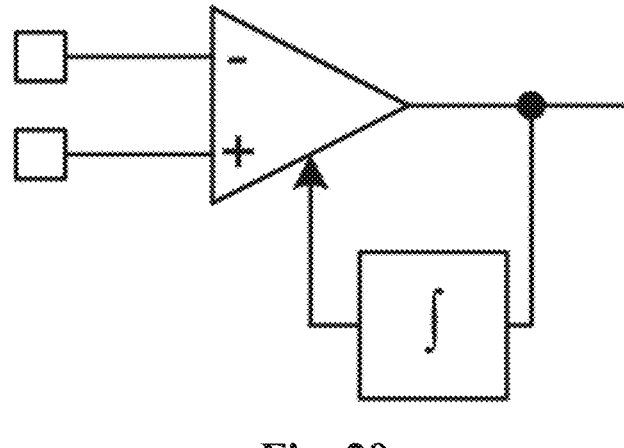
FIG. 29 depicts measurement circuitry for making differential ECAP measurements with crosstalk compensation in accordance with a further embodiment of the invention.

It is again noted that the stimulus crosstalk compensation need not be perfect: it is only necessary to ensure that the ECAP amplifier does not clip during the recording. Residual crosstalk can be subtracted in software (e.g. by subtracting the DC component, for constant compensation). Thus it is possible to use the output from an ECAP amplifier to estimate the crosstalk as it changes. For example, the average output level of the amplifier will indicate in which direction and how much the compensation signal needs to be adjusted, so an integrator can be used to adjust it. Such a system might only update the compensation signal in between stimulus phases, or might be combined with other predictive sources. FIG. 29 illustrates such an embodiment, which involves integrating the ECAP amplifier output to derive a compensation signal. This drives the compensation signal such that the average of the ECAP amplifier output is zero.

Given the generally resistive nature of the tissue, the crosstalk voltage can be expected to vary linearly with the stimulation current. This is also informative to predictions of crosstalk, as knowledge of the stimulus current waveform can be used to predict the crosstalk voltage waveform, and consequently the necessary compensation waveform.

A further source of information available in the device can be obtained by recording the voltage on the stimulus electrode and using that to determine a suitable crosstalk cancellation signal to compensate for crosstalk on the recording electrode(s).

Figure 30:
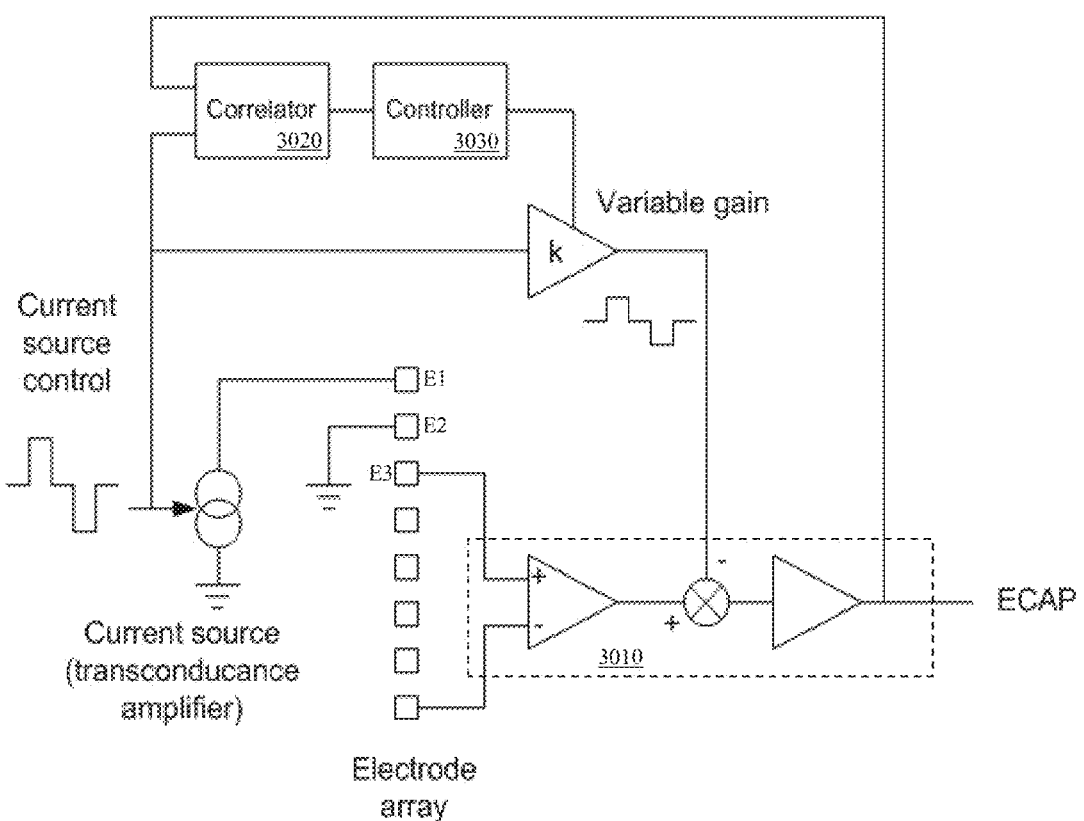
FIG. 30 depicts measurement circuitry for making differential ECAP measurements with crosstalk compensation in accordance with yet a further embodiment of the invention.

FIG. 30 illustrates a further embodiment of the invention. When stimulating on E1 and E2, at a minimum in current hardware it is expected that at least around 18 dB of stimulus crosstalk reduction will be required to bring the signal dynamic range from E3 below 96 dB. Use of the aforementioned techniques permits use of a feedforward technique for stimulus crosstalk cancellation. In this embodiment, the signal at the output of the differential front-end 3010 is compared to the stimulus by use of a correlator 3020, which estimates the amount of crosstalk present in the ECAP amplifier output. This estimate is fed to a controller 3030, which for example may be an integrator, that adjusts the feed-forward gain k from the current source control and nulls the stimulus crosstalk by subtraction of the compensating signal in between the two gain stages.

The crosstalk estimate also provides information on changes in geometric factors around the electrodes. For example, the gain estimate k describes the electrical transimpedance between the stimulating (E1) and recording (E3) electrodes. In an SCS context, this would depend on the distance between the spinal cord and the electrode array. Consequently, this estimated gain signal could be fed into an SCS therapy controller (not shown) to improve its performance, for example to adjust an SCS current control loop gain or target to maintain constant neural recruitment.

The coupling between stimulation and return electrodes typically varies according to some physical process, and so can be predicted using any one of the many open- or closed-loop methods used for physical processes. For example, a PID controller can be used to adjust a compensating signal to zero out the crosstalk voltage at the output of a compensating amplifier.

Where non-constant compensation is desired, the crosstalk waveform can be estimated, for example using a dedicated ADC or the ECAP amplifier output. Care must be taken not to inadvertently measure and compensate out the ECAP signal itself. To this end, use of a model of the crosstalk signal to avoid overfitting may be desirable. For example, if the electrode is represented as one or more CPEs, the CPE parameters may be fitted, and the corresponding waveform calculated for compensation.

Further embodiments of the invention may further provide for additional enhancements. One such enhancement is noise compensation. During a stimulus, the voltage observed at the recording electrode varies with the current through the stimulating electrodes. The current may not be exactly constant; current sources are subject to noise processes like all electronics, and so the current waveform may be noisy which leads to noise in the voltage observed at the recording electrode.

Thus, in some embodiments the actual stimulus current can be measured or estimated, for example by measuring the voltage at the stimulation or recording electrodes, by using a current sense circuit to measure the actual current delivered, or by using a model to predict the variation in current during constant voltage stimulation. This current measurement can be mixed in to the crosstalk compensation signal in order to compensate out the variation in stimulus current, in a non-constant compensation system. Alternatively, if the current variation is not so large as to cause clipping, this compensation can be performed later in the signal chain, for example using DSP techniques after digitisation. This is applicable to both constant and non-constant compensation techniques.

To demonstrate some of the above-described principles of stimulus crosstalk compensation, experiments were conducted in which an amplifier was built which is capable of recording during the stimulus. The amplifier topology used for this experiment is as shown in FIG. 25a. As noted above this amplifier uses an analog integrator 2510 to perform a compensation measurement at every current transition in the stimulus, which suspends recording for approximately 70 μs each time. The amplifier has a gain of 50, which is capable of directly driving an ADC for acquiring ECAP data. The configuration of FIG. 14 was applied in this experiment to a saline environment. A standard SCS neuromodulation lead, with 12 electrodes, was suspended in 1/10 normal saline, representing a patient's tissues. A biphasic stimulus of 7 mA was applied in bipolar manner between electrodes E1 and E2. The stimulus voltage was approximately 7 volts.

The pulse width was 800 μs and repeated at 50 Hz, in range for a standard human therapeutic SCS stimulus. Virtual ground driver 1410 was used to minimise the common-mode voltage of the stimulus; the reference electrode was E7, and this electrode also acted as the reference electrode for recordings. A 50 μV peak-to-peak 4 kHz sine wave was injected in series with the amplifier input, representing a low-amplitude physiological signal which it is desired to record.

To understand the magnitude of the problem of stimulus crosstalk, the stimulus voltage was experimentally recorded between each of the free electrodes, with results shown in Table 1.

TABLE 1

Peak-to-peak stimulus crosstalk voltage measured during the stimulus pulse between different recording electrodes, without crosstalk compensation (mV)

| | E4 | E5 | E6 | E7 | E8 | E9 | E10 | E11 | E12 |
|---|---|---|---|---|---|---|---|---|---|
| E3 | 298 | 372 | 403 | 418 | 426 | 431 | 434 | 436 | 437 |
| E4 | | 74 | 105 | 120 | 128 | 133 | 136 | 138 | 139 |
| E5 | | | 31 | 46 | 54 | 59 | 62 | 64 | 65 |
| E6 | | | | 15 | 23 | 28 | 31 | 33 | 34 |
| E7 | | | | | 8 | 13 | 16 | 18 | 19 |
| E8 | | | | | | 4 | 7 | 10 | 11 |
| E9 | | | | | | | 3 | 5 | 6 |
| E10 | | | | | | | | 2 | 3 |
| E11 | | | | | | | | | 1 |

To understand the magnitude of the stimulus crosstalk problem reflected in Table 1, these figures can be compared to a commercially available ECAP-recording implantable device which has a maximum input range of 2.4 mV peak-to-peak without clipping. For this 7 mA stimulus, the commercially available device would be limited to recording between E11-E12 only. At higher stimulus currents, the crosstalk voltage differences of Table 1 would increase, and recording during stimulus would be entirely impossible on all electrodes. This is undesirable, not just because a reduced choice of electrodes limits therapeutic options, but because the quality of ECAP recording depends on the distance between the recording and reference electrodes: electrodes that are closer together will see more similar potentials at each point in time, reducing the amplitude of the recorded signal.

Figure 31:
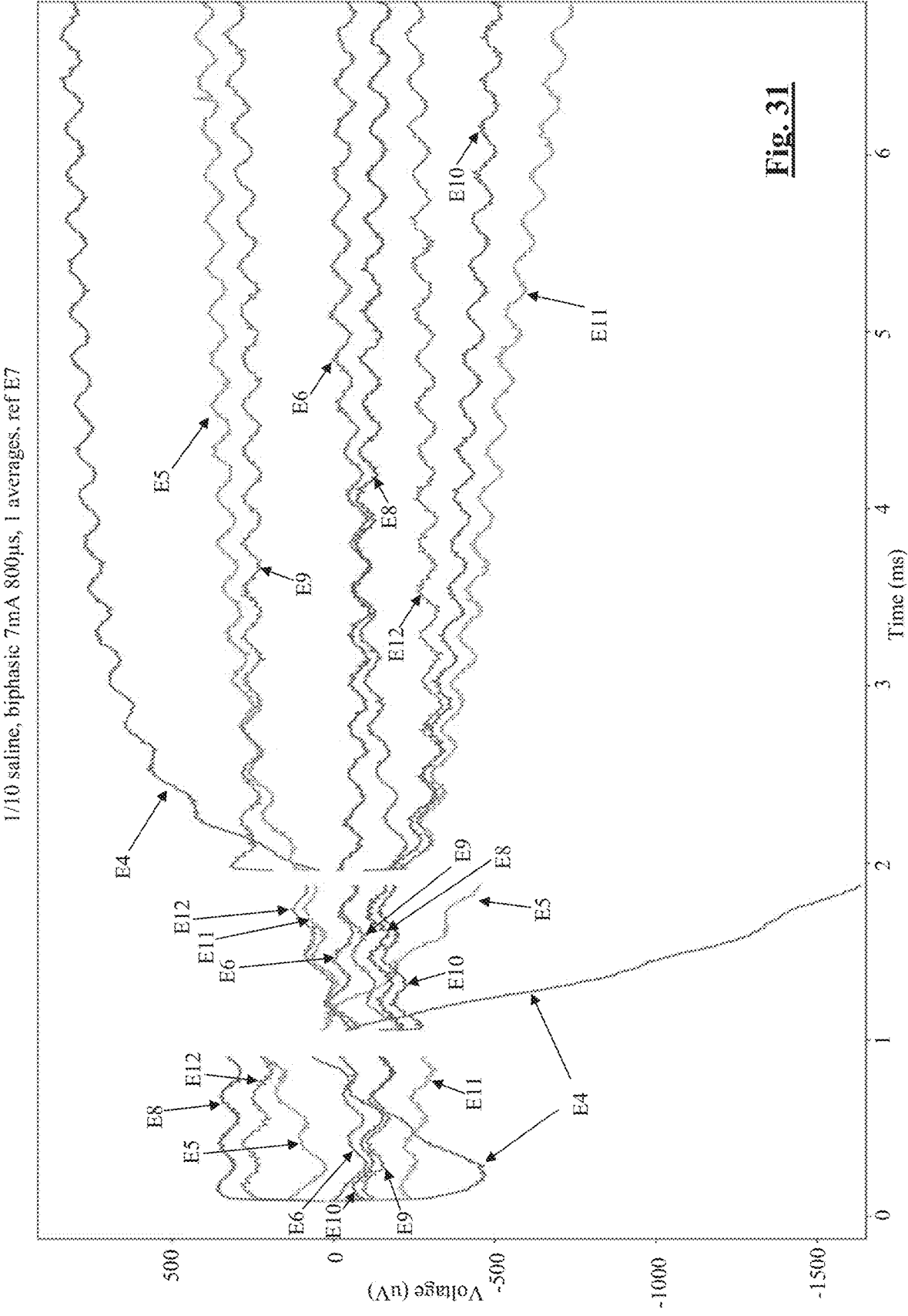
FIGS. 31 and 32 are plots of results from experimental implementation of the embodiment of FIGS. 25a and 25b.

To illustrate the benefits of the experimental implementation FIGS. 14 and 25, recording was performed experimentally, in sequence, on each of the free electrodes. The results are shown in FIG. 31. As noted above, the absence of data at certain times in each trace is because recording is suspended for approximately 70 μs at every current transition in the stimulus. No recordings were obtained for E1 or E2 (the stimulating electrodes), nor E3 (which in this arrangement could not be adequately compensated), nor E7 (the reference electrode).

Periods where the compensation measurement was being actively updated, preventing the amplifier from recording input, are blanked in FIG. 31. The voltage arising on electrode E4 remains between about +700 μV and −1600 μV, and is thus kept within the maximum input range of 2.4 mV by use of the crosstalk compensation of FIG. 25. All other recordings remain within an even smaller range. In addition to the sinusoidal signal of interest, some undesirable residual stimulus artefact remains on the electrodes, particularly E4 and E5, as seen in the decaying excursions of these recordings. However, as these unwanted artefacts components are kept within the input range of the amplifier chain by virtue of the application of stimulus crosstalk cancellation, such unwanted components can be removed digitally via DSP techniques if required. As desired, the 50 μV sinusoidal 4 kHz signal can be observed and thus easily retrieved from all recordings. Indeed, for the recordings from E6 and E8-E12 the sinusoidal signal of interest can be directly resolved without further processing.

Accordingly, FIG. 31 reveals that the stimulus crosstalk cancellation effected by the embodiment of FIG. 25 is sufficient that the commercial ECAP-recording implantable device would be able to measure ECAPs between any pair of electrodes, providing for significantly improved recording ability and therapeutic flexibility. This would also extend to operation with stimulus currents at least 3 times larger than those examined here, for all recording electrodes except E4.

Figure 32:
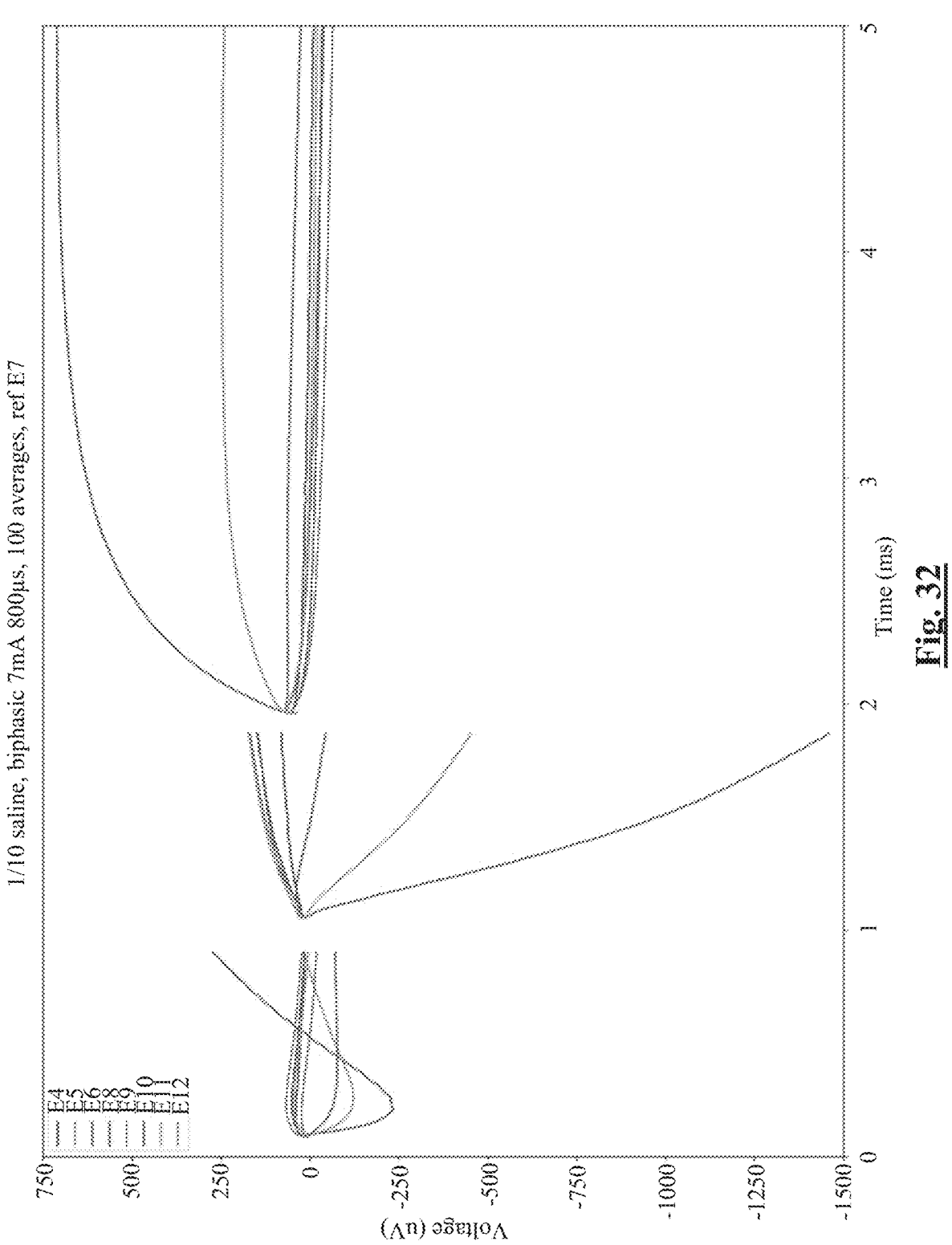

To investigate the repeatability of the results shown in FIG. 31, the experiment was repeated 100 times and averaged, with no "ECAP" insertion. FIG. 32 is a plot of the averaged results, showing that the underlying artefact is consistent and thus removable by the present methods.

Figures 33, 34:
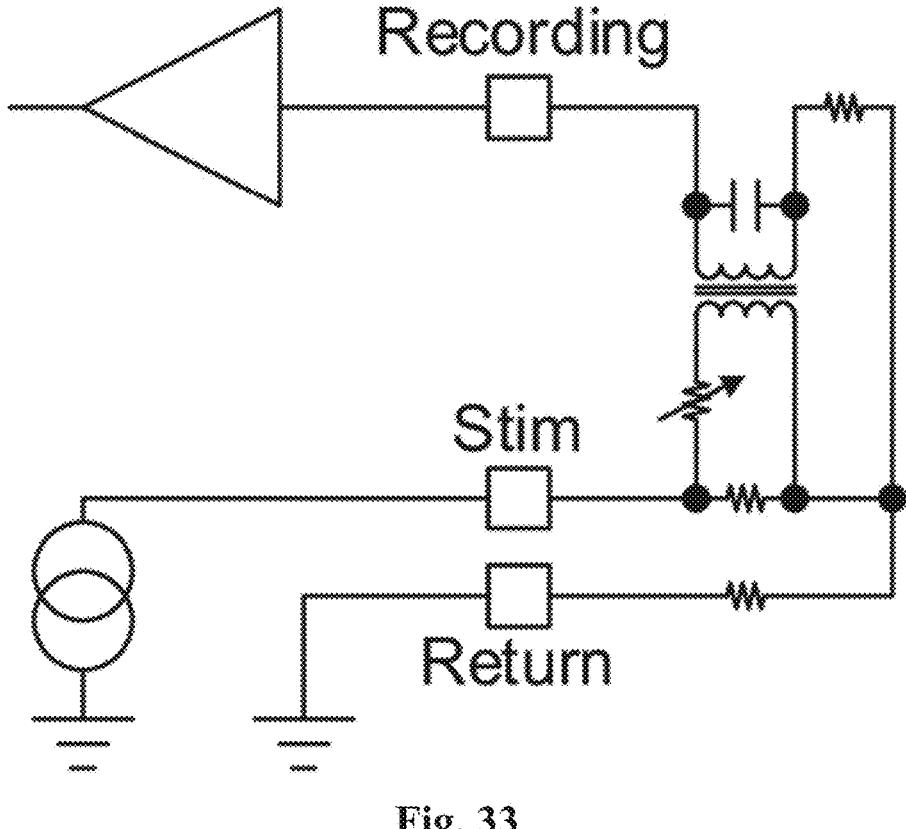
FIG. 33 illustrates an experimental configuration for recording during stimulation of a harmonic load.
FIG. 34 is a plot of results obtained from the experiment of FIG. 33.

To further investigate the utility of recording during stimulation, a harmonic load is used to test the basic functionality of this ECAP recording system. FIG. 33 illustrates the experimental configuration for recording during stimulation of a harmonic load. Only the used electrodes of the load are shown. A passive ground stimulation configuration is used (E2 connected to ground). The return electrode acts as the measurement reference electrode. The harmonic load consists of a resistive star network, with 500 ohm resistors from each electrode connection to a common star point. This acts as a simple simulation of the resistive component of a tissue impedance, and does not include the electrode-tissue interface. In order to simulate an ECAP, a harmonic circuit is used. This uses a transformer and capacitor to produce an oscillating signal which resembles an ECAP. The transformer is excited by the voltage across one of the star resistors, which in turn is driven by the stimulus current. The resulting oscillatory voltage is then superimposed on the recording electrode using the other winding of the transformer. The gain of the oscillating signal can be adjusted using the variable resistor.

Due to the star network used in FIG. 33, the voltage at the recording electrode swings by half of the stimulation voltage. In this experiment, the stimulation current was 12 mA, so the signal at the recording electrode swings by ±6 V during the stimulation. Clearly this far exceeds the capabilities of a single-ended, uncompensated ECAP measurement amplifier.

On the other hand, when the recording configuration of FIG. 25 is introduced into the stimulus configuration of FIG. 33, the signal at the recording electrode is kept within an acceptable range, except during stimulus transients, as shown in FIG. 34. The two traces in FIG. 34 correspond to two different settings of the variable resistor in FIG. 33, to mimic a "small" ECAP and a "large" ECAP. These oscillatory responses are only of the order of tens of μV, but are clearly observable both during the first and second stimulus phases, and also in the period after the stimulus, despite the large transients between phases. Once again this experiment demonstrates the efficacy with which the embodiment of FIG. 25 is able to record μV range neural responses even during the application of large (7-12 mA, 6-7 V) stimulus pulses.

It is noted that recording of neural responses during or immediately after a stimulus presents a range of benefits. For example, such measurements might allow the neural response to be observed during application of a long, essentially DC, pulse. Such a pulse pre-polarises the neural membrane and, if the pulse amplitude is slowly incremented, once the pulse amplitude reaches the rheobase then an ECAP will occur and by virtue of the present invention can be observed. Thus, recording the neural response during application of the stimulus may permit direct measurement of rheobase. There are also many circumstances where therapeutically beneficial neurostimulation involves the application of stimuli which are of a duration which causes the stimulus to partly or entirely overlap with the recruited response. Accordingly, being able to record the neural response during application of the stimulus will reveal a leading portion or even the entirety of the evoked response in such circumstances.

Figure 35:
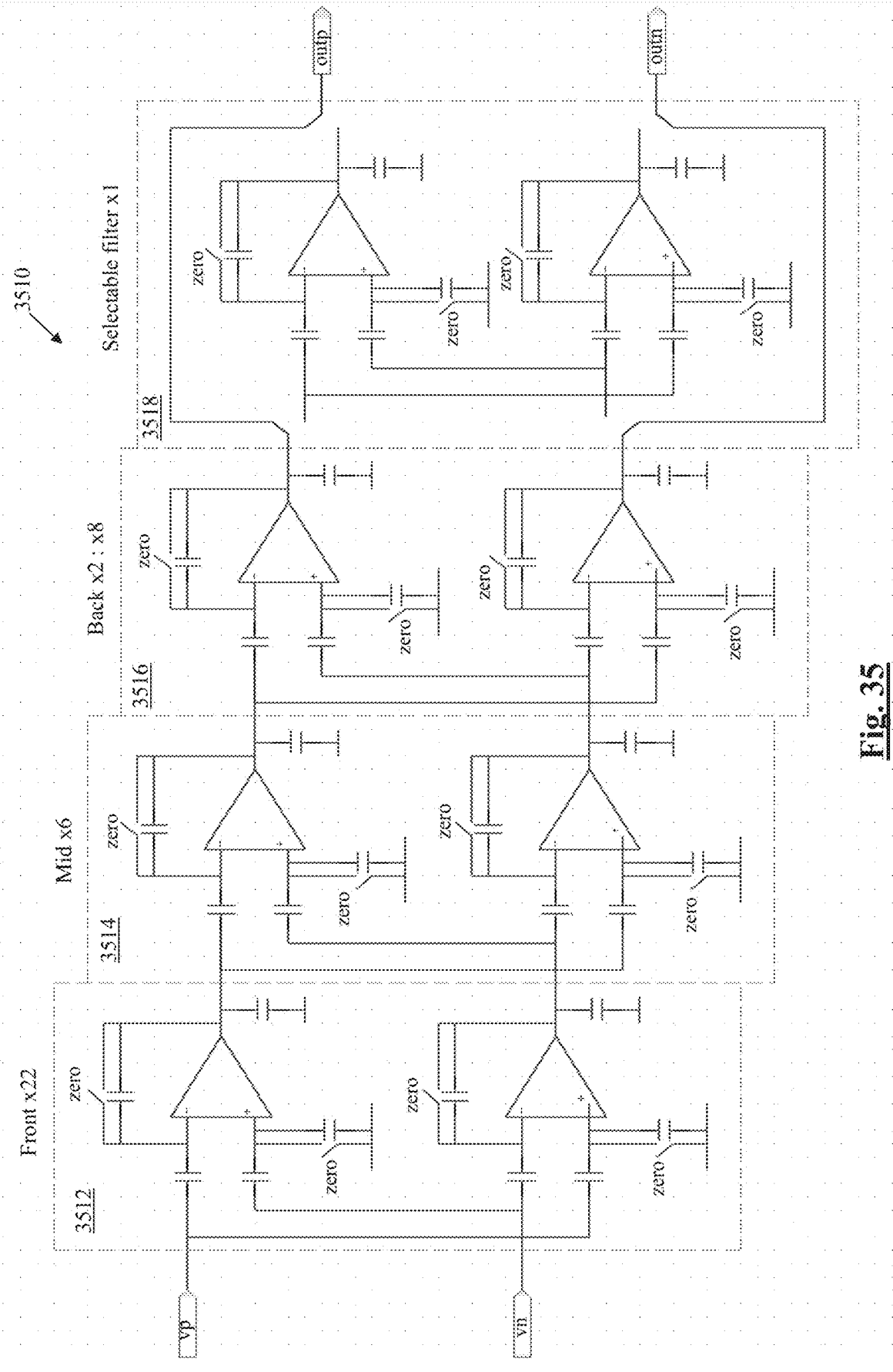
FIG. 35 is a circuit diagram of a multistage on-chip measurement amplifier in accordance with another embodiment of the invention.

FIG. 35 illustrates another embodiment of the invention, comprising an ECAP amplifier implemented on a single chip as part of a neuromodulation system. In FIG. 35 an on-chip ECAP amplifier 3510 measures the voltage between vp and vn and delivers the output as a differential signal between outp and outn. Amplifier 3510 has three gain stages, a front stage 3512 providing a gain of 22, a mid stage 3514 providing a gain of 6, and a back stage 3516 providing a gain of 8. Amplifier 3510 also comprises a selectable filter 3518 with unity gain.

This amplifier 3510 contains a set of zeroing switches, each denoted "zero" in FIG. 35. When these switches are closed, the output of each individual amplifier is zero. Operation of the zeroing switches thus permits the amplifier 3510 to be blanked at times when desired, such as to effect transient blanking. Moreover, during such blanking periods, the various series capacitors in the device are driven to suitable compensating voltages. Thus, this embodiment compensates for stimulus crosstalk by placing the amplifier into zeroing for a certain period at the leading edge of each stimulus phase, in order to acquire suitable compensating voltages upon the series capacitors. Then the zeroing is released, and ECAP recording can proceed. In this embodiment, the zeroing period is approximately 40 μs.

Figure 36:
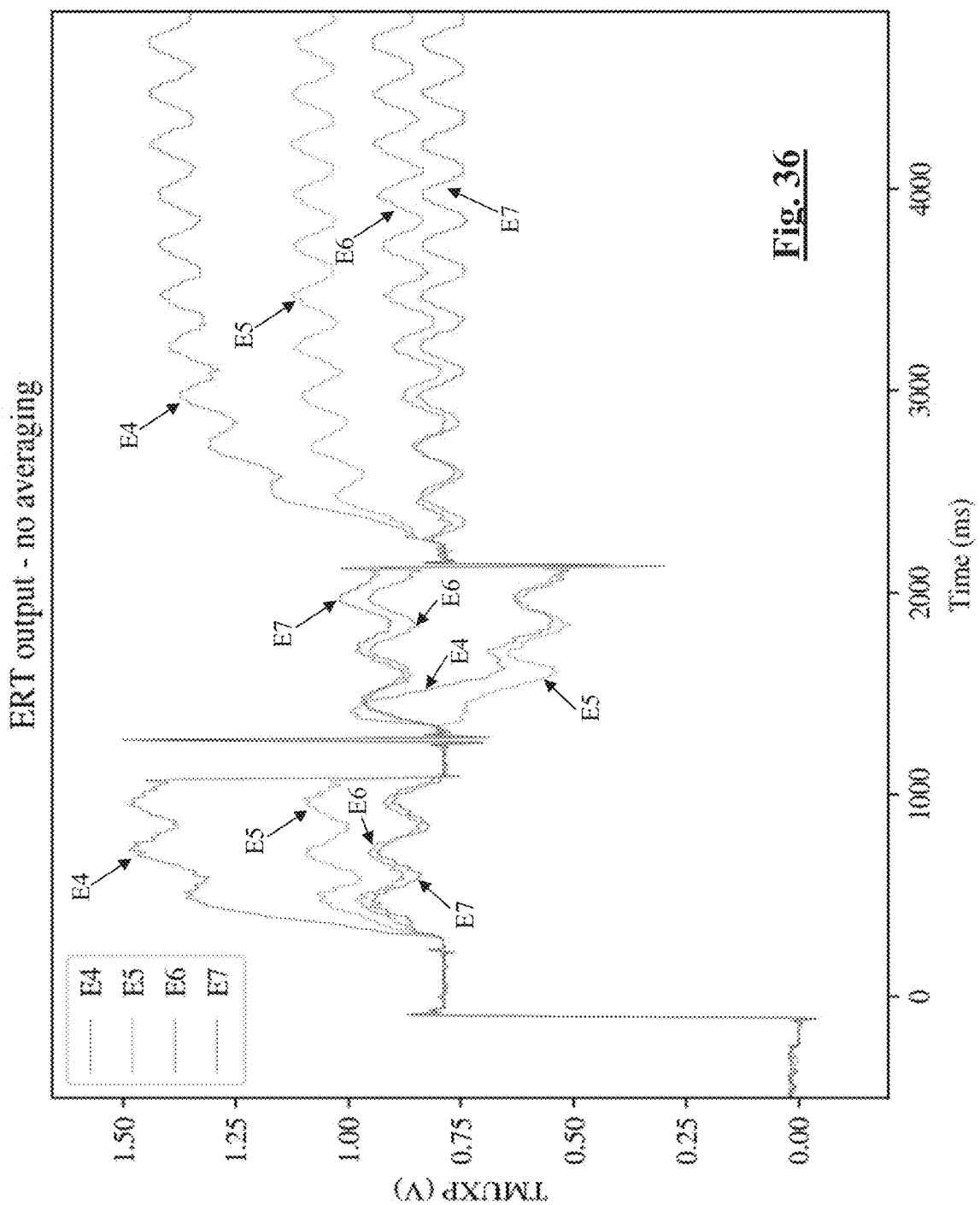
FIG. 36 is a plot of a recording obtained experimentally in a saline bath using the amplifier of FIG. 35.

FIG. 36 illustrates recordings obtained with the implantable ECAP amplifier 3510 in a 1/10 saline bath. A biphasic stimulus of pulse width approximately 800 μs and current 3 mA was delivered between electrodes E1-E2. A test signal comprising a 4 kHz sinusoid of amplitude 200 μV peak to peak was superimposed on each recording electrode, in the manner described previously herein. Recordings obtained on electrodes E4 to E7 are shown. As can be seen in FIG. 36, a uV-range signal can be observed, and thus the efficacy of neural recruitment can be assessed, both during the stimulus (0-2000 ms) and after the stimulus (approx. 2300-5000 ms), even when large stimulus crosstalk is present.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

The invention claimed is:

1. A device for recording evoked neural responses, the device comprising:

a plurality of electrodes including one or more nominal stimulus electrodes and one or more nominal sense electrodes;

a stimulus source for providing a stimulus to be delivered from the one or more stimulus electrodes to a neural pathway in order to give rise to an evoked action potential on the neural pathway;

measurement circuitry for recording a neural compound action potential signal sensed at the one or more sense electrodes; and crosstalk cancellation circuitry configured to produce a stimulus crosstalk cancellation signal, the crosstalk cancellation circuitry further configured to inject the stimulus crosstalk cancellation signal during delivery of the stimulus into the measurement circuitry, the stimulus crosstalk cancellation signal being configured to cancel a stimulus crosstalk voltage arising upon the one or more sense electrodes as a result of delivery of the stimulus.

2. The device of claim 1 wherein the stimulus crosstalk cancellation signal is injected into the measurement circuitry prior to analog-to-digital conversion of the neural compound action potential signal.

3. The device of claim 1 wherein the stimulus crosstalk cancellation signal is injected into the measurement circuitry prior to high gain amplification of the neural compound action potential signal.

4. The device of claim 1 wherein the stimulus comprises one or more stimulus phases each comprising a pulse of constant current, and wherein the pulse of constant current is delivered by a first stimulus electrode and a return electrode is driven by a virtual ground circuit which seeks to drive a sense electrode voltage to ground, and wherein the stimulus crosstalk cancellation signal is configured to take a respective constant value during each stimulus phase, the constant value of the stimulus crosstalk cancellation signal being selected to cancel the stimulus crosstalk voltage arising upon the one or more sense electrodes as a result of delivery of the pulse of constant current.

5. The device of claim 1 further configured to provide for non-constant compensation in order to cancel a non-constant stimulus crosstalk voltage arising upon the one or more sense electrodes as a result of delivery of the stimulus.

6. The device of claim 5, wherein non-constant compensation is applied to cancel a non-constant stimulus crosstalk voltage arising as a result of use of one or more sense electrodes to pass current during delivery of the stimulus.

7. The device of claim 1 wherein the stimulus crosstalk cancellation signal is configured based on measurements of stimulus crosstalk.

8. The device of claim 1 wherein the stimulus crosstalk cancellation signal is configured based on predictions of expected stimulus crosstalk, the predictions being made using a model.

9. The device of claim 8 further configured to update the model iteratively over time based on observed performance of the stimulus crosstalk cancellation signal over multiple stimuli.

10. The device of claim 1 wherein the device is operable to configure the stimulus crosstalk cancellation signal so as to cancel predicted or observed components of stimulus crosstalk arising in the measurement circuitry as a result of resistive coupling via tissue between the electrodes.

11. The device of claim 1 wherein the device is operable to configure the stimulus crosstalk cancellation signal so as to cancel predicted or observed components of stimulus artefact arising in the measurement circuitry as a result of accumulated charge in electrode-tissue interface layers as a function of position along each electrode of the plurality of electrodes.

12. The device of claim 1 wherein the device is operable to configure the stimulus crosstalk cancellation signal so as to cancel predicted or observed components of stimulus artefact arising in the measurement circuitry as a result of non-infinite common-mode rejection of amplifier ground signal variations caused by accumulated charge in electrode-tissue interface layers of a stimulus return electrode.

13. The device of claim 1 wherein the measurement circuitry comprises a measurement amplifier configured to obtain a single-ended recording of a neural compound action potential signal sensed at one sense electrode.

14. The device of claim 13 wherein the sense electrode is connected to a first input of the measurement amplifier, and a second input of the measurement amplifier is connected to a midpoint of a resistive chain, the resistive chain extending between an output of the measurement amplifier and a stimulus crosstalk cancellation voltage injection input.

15. The device of claim 14 wherein a ratio R of resistance either side of the midpoint in the resistive chain is used to derive a desired stimulus crosstalk cancellation signal, by multiplying a measured or predicted stimulus crosstalk by R.

16. The device of claim 1 wherein the measurement circuitry comprises a differential amplifier configured to obtain a differential recording of a neural compound action potential signal sensed at two sense electrodes.

17. The device of claim 16 wherein a first input of the differential amplifier is connected to an output of the differential amplifier via a feedback element, and a second input of the differential amplifier is resistively connected to a stimulus crosstalk voltage injection input.

18. The device of claim 1 wherein the or each sense electrode is connected to the measurement circuitry via a respective input buffer amplifier.

19. The device of claim 1, further configured to blank the measurement circuitry during one or more stimulus transients.

20. The device of claim 1, further configured to blank the measurement circuitry during an initial portion of the stimulus, and to thereafter unblank the measurement circuitry at a time which is adaptively controlled.

21. The device of claim 20 wherein the time is adaptively controlled based on one or more past observations of time(s) at which neural responses arise relative to the stimulus.

22. The device of claim 1 wherein the recording of the neural compound action potential signal comprises a plurality of discontinuous recorded segments.

23. The device of claim 22 wherein a segmented matched filter ECAP detector having segments corresponding temporally to the recorded segments is applied to the recorded segments to determine recruitment information.

24. The device of claim 22 wherein interpolation is applied to the plurality of discontinuous recorded segments in order to estimate a neural response profile during blanking periods between the recorded segments.

25. The device of claim 24 further configured to process the recording of the neural compound action potential signal in order to assess an efficacy of the stimulus.

26. The device of claim 25 further comprising feedback loop circuitry which controls application of a subsequent stimulus based on the determined efficacy of the stimulus.

27. A method for recording evoked neural responses, the method comprising:

delivering a stimulus from one or more stimulus electrodes to a neural pathway in order to give rise to an evoked action potential on the neural pathway;

recording, with measurement circuitry, a neural compound action potential signal sensed at one or more sense electrodes; and injecting a stimulus crosstalk cancellation signal into the measurement circuitry during delivery of the stimulus, the stimulus crosstalk cancellation signal being configured to cancel a stimulus crosstalk voltage arising upon the one or more sense electrodes as a result of delivery 5 of the stimulus.

28. A non-transitory computer readable medium for recording evoked neural responses, the non-transitory computer readable medium comprising computer program code means for: 10 causing delivery of a stimulus from one or more stimulus electrodes to a neural pathway in order to give rise to an evoked action potential on the neural pathway;

causing recording, with measurement circuitry, of a neural compound action potential signal sensed at one or more 15 sense electrodes; and causing injection of a stimulus crosstalk cancellation signal into the measurement circuitry during delivery of the stimulus, the stimulus crosstalk cancellation signal being configured to cancel a stimulus crosstalk voltage 20 arising upon the one or more sense electrodes as a result of delivery of the stimulus.

\* \* \* \* \*